(12) United States Patent
Cheng et al.

(10) Patent No.: US 6,498,242 B1
(45) Date of Patent: Dec. 24, 2002

(54) BIOLOGICAL METHOD FOR THE PRODUCTION OF ADIPIC ACID AND INTERMEDIATES

(75) Inventors: Qiong Cheng, Wilmington, DE (US); Vasantha Nagarajan, Wilmington, DE (US); Stuart M. Thomas, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/648,004

(22) Filed: Jul. 14, 1999

Related U.S. Application Data

(63) Continuation-in-part of application No. 09/252,553, filed on Feb. 19, 1999, now abandoned.

(51) Int. Cl.$^7$ .......................... C07H 21/04; C12N 9/00
(52) U.S. Cl. .................. 536/23.2; 435/142; 435/183; 435/189; 435/190; 435/195; 536/23.1; 536/23.7; 530/350
(58) Field of Search .................. 435/142, 183, 435/189, 190, 195; 536/23.1, 23.2, 23.7; 530/350

(56) References Cited

U.S. PATENT DOCUMENTS

| | | | |
|---|---|---|---|
| 3,843,466 A | 10/1974 | Akabori et al. | 195/28 |
| 4,400,468 A | 8/1983 | Faber | 435/142 |
| 5,616,496 A | 4/1997 | Frost et al. | 435/252.3 |
| 5,629,190 A | 5/1997 | Petre et al. | 435/227 |
| 5,635,391 A | 6/1997 | Petre et al. | 435/252.3 |

FOREIGN PATENT DOCUMENTS

| | | |
|---|---|---|
| JP | 7403156 | 11/1974 |
| JP | 61128890 | 6/1986 |
| JP | 01023894 A2 | 1/1989 |
| JP | 01023895 A2 | 1/1989 |

OTHER PUBLICATIONS

Chen et al., GenEmbl database, Accession No. M19029, Apr. 1993.*
Frost, John, Chem. Eng. Rugby, Engl. (1996) 611, 32–35.
Steinbuechel, Alexander CLB Chem. Labor Biotech. (1995) 46(6) 277–8.
Draths et al., ACS Symp. Ser. (1994), 577 (Benign by Design) 32–45.
Cho, Takeshi et al., Bio Ind. (1991), 8(10), 671–8.
Hasegawa et al., Biosci., Biotechnol., Biochem. (1992), 56(8), 1319–20.
Yoshizako et al., J. Ferment. Bioeng. (1989), 67(5), 335–8.
Kim et al., Sanop Misaengmul Hakhoechi (1985), 13(1), 71–7.
Donoghue et al., Eur. J. Biochem. (1975), 60(1), 1–7.
Tanaka et al., Hakko Kagaku Kaishi (1977), 55(2), 62–7.
Chen et al., J. Bacteriol., 170, 781–789 (1988).
Junker et al, J. Bacteriol. 179 (3), 919–927 (1997).
Nagata et al., J. Bacteriol 176 (11), 3117–3125 (1994).
Ammendola et al., Biochemistry 31(49), 12514–12523(1992).
Raibaud et al., J. Bacteriol. 173(14), 4454–4463(1991).

* cited by examiner

*Primary Examiner*—Rebecca E. Prouty
*Assistant Examiner*—Richard Hutson

(57) ABSTRACT

A gene cluster has been isolated from an Acinetobacter sp. that encodes the enzymes expected to convert cyclohexanol to adipic acid. The entire gene cluster has been cloned and all open reading frames have been sequenced. Cosmid clones have been identified containing the gene cluster. Demonstration of conversion of cyclohexanol to adipic acid has been made with the recombinant *E. coli* host strain containing the cosmids.

1 Claim, 3 Drawing Sheets

SEQUENCE LISTING

<160> NUMBER OF SEQ ID NOS: 32

<210> SEQ ID NO 1
<211> LENGTH: 543
<212> TYPE: DNA
<213> ORGANISM: Acinetobacter sp.

<400> SEQUENCE: 1

```
atgacgattc aaaaaatggc cttgattggc acaggcgtaa tgggaatggg tattgcgcaa      60
attgcagcac aggcgggtgt tgaggtccgt ttatttgatg ctaaacccgg cgctgctgag     120
caaggcttgg aaaaattaaa agtaaccttg cacaaactag ctgctaaagg aaagttaacc     180
gaacagcagc ttgtggatac cttagcccga ttgattatct tggaaagcat tgaagaggtt     240
gctggcgttg atctggtcgt agaagcaatt attgaaaatc tggaaatcaa gcaaactttg     300
tttaaacagc ttgaaaggat tgtggctgaa gaaactattc tggtttcaaa tacatcctca     360
ctatctgtga cctcaattgc atctgcgtgt cagcatcagg gccgtatcgc aggtttccat     420
ttcttcaatc cggttccact gatgaaaatt gtggaagtga ttgcggggtt ggctacagat     480
gagcaagtcg tagtcgactt actggatctg gcgaccgcat gggactttgg gtgtccggac     540
taa                                                                  543
```

<210> SEQ ID NO 2
<211> LENGTH: 180
<212> TYPE: PRT
<213> ORGANISM: Acinetobacter sp.

<400> SEQUENCE: 2

```
Met Thr Ile Gln Lys Met Ala Leu Ile Gly Thr Gly Val Met Gly Met
  1               5                  10                  15

Gly Ile Ala Gln Ile Ala Ala Gln Ala Gly Val Glu Val Arg Leu Phe
                 20                  25                  30

Asp Ala Lys Pro Gly Ala Ala Glu Gln Gly Leu Glu Lys Leu Lys Val
             35                  40                  45

Thr Leu His Lys Leu Ala Ala Lys Gly Lys Leu Thr Glu Gln Gln Leu
         50                  55                  60

Val Asp Thr Leu Ala Arg Leu Ile Ile Leu Glu Ser Ile Glu Glu Val
 65                  70                  75                  80

Ala Gly Val Asp Leu Val Val Glu Ala Ile Ile Glu Asn Leu Glu Ile
                 85                  90                  95

Lys Gln Thr Leu Phe Lys Gln Leu Glu Arg Ile Val Ala Glu Glu Thr
                100                 105                 110

Ile Leu Val Ser Asn Thr Ser Ser Leu Ser Val Thr Ser Ile Ala Ser
             115                 120                 125
```

```
Ala Cys Gln His Gln Gly Arg Ile Ala Gly Phe His Phe Asn Pro
        130                 135                 140

Val Pro Leu Met Lys Ile Val Glu Val Ile Ala Gly Leu Ala Thr Asp
145                 150                 155                 160

Glu Gln Val Val Ser Thr Tyr Trp Ile Trp Arg Pro His Gly Thr Leu
                165                 170                 175

Gly Val Arg Thr
            180

<210> SEQ ID NO 3
<211> LENGTH: 777
<212> TYPE: DNA
<213> ORGANISM: Acinetobacter sp.

<400> SEQUENCE: 3
atggaaaatg aaatattgaa tttagatatt caaagtaatg gtgtggccat tgttgaacta      60
catcgtccag atactagaaa tgcattgaat ctggaactgc gccaacagct cgcagcaatg    120
tttgagcagc tcgctgcatc tgatacagtc cgcgcaattg tcattactgg tggtgaaaaa    180
gtatttgcag caggtgcgga tatccgggac ttcaccactg caaaaaccgt agacatgtat    240
ttacgccata cggaacagta ctggcgggcc attattgatt gccctaaacc gattgtggct    300
gctgtgaatg gatatgcatt gggtggtggg tgtgaacttg caatgcatgc agacatcatt    360
attgccggaa aatcagccca gtttggtcag cctgaagtca aattgggggct gatgccaggt    420 gctggtggta cccaacgctt actgcgtgcg gtagggaagt ttaaagccat gcaaatagtg    480
ttaacaggaa agatcttttc tgcagaagaa gctgacaaaa tggggttggt ttccgaagtg    540
gttgaggatg atcaaaccct tgctaaagcg gttgaaattg cgacacagat tgcccaactc    600
tcaccgattg ccgttgaaca gatcaaagaa gtcacaacac taggtgccaa tgccactc     660 gatggtgctt tggcattaga gcgtaaagcc ttccaaattt tatttgatac acaagatcaa    720
aaagaaggcg tcaatgcctt tttcgaaaag cgaagccctc aatatcaagg aaaataa      777

<210> SEQ ID NO 4
<211> LENGTH: 258
<212> TYPE: PRT
<213> ORGANISM: Acinetobacter sp.

<400> SEQUENCE: 4

Met Glu Asn Glu Ile Leu Asn Leu Asp Ile Gln Ser Asn Gly Val Ala
  1               5                  10                  15

Ile Val Glu Leu His Arg Pro Asp Thr Arg Asn Ala Leu Asn Leu Glu
                 20                  25                  30

Leu Arg Gln Gln Leu Ala Ala Met Phe Glu Gln Leu Ala Ala Ser Asp
             35                  40                  45

Thr Val Arg Ala Ile Val Ile Thr Gly Gly Glu Lys Val Phe Ala Ala
         50                  55                  60

Gly Ala Asp Ile Arg Asp Phe Thr Thr Ala Lys Thr Val Asp Met Tyr
 65                  70                  75                  80

Leu Arg His Thr Glu Gln Tyr Trp Arg Ala Ile Ile Asp Cys Pro Lys
                 85                  90                  95

Pro Ile Val Ala Ala Val Asn Gly Tyr Ala Leu Gly Gly Gly Cys Glu
                100                 105                 110

Leu Ala Met His Ala Asp Ile Ile Ile Ala Gly Lys Ser Ala Gln Phe
            115                 120                 125

Gly Gln Pro Glu Val Lys Leu Gly Leu Met Pro Gly Ala Gly Gly Thr
```

```
            130                 135                 140
Gln Arg Leu Leu Arg Ala Val Gly Lys Phe Lys Ala Met Gln Ile Val
145                 150                 155                 160

Leu Thr Gly Lys Ile Phe Ser Ala Glu Glu Ala Asp Lys Met Gly Leu
                165                 170                 175

Val Ser Glu Val Val Glu Asp Asp Gln Thr Leu Ala Lys Ala Val Glu
            180                 185                 190

Ile Ala Thr Gln Ile Ala Gln Leu Ser Pro Ile Ala Val Glu Gln Ile
                195                 200                 205

Lys Glu Val Thr Thr Leu Gly Ala Asn Met Pro Leu Asp Gly Ala Leu
210                 215                 220

Ala Leu Glu Arg Lys Ala Phe Gln Ile Leu Phe Asp Thr Gln Asp Gln
225                 230                 235                 240

Lys Glu Gly Val Asn Ala Phe Phe Glu Lys Arg Ser Pro Gln Tyr Gln
                245                 250                 255

Gly Lys

<210> SEQ ID NO 5
<211> LENGTH: 1155
<212> TYPE: DNA
<213> ORGANISM: Acinetobacter sp.

<400> SEQUENCE: 5
atgattcgcg atcaagacac attaaatcag ctggttgaca tgatccgtca gtttgtcgat      60
ggcgttctta ttcccaatga agaaattgtt gcggaaaccg atgaaattcc agctgaaatc    120
gtgcagcaaa tgaaagaact gggtcttttt ggtctcacca ttcctgagga atatgagggt    180
cttggcctga ccatggagga agaggtttac attgcatttg aactgggacg tacctctcct    240
gctttccgtt cactgatcgg cactaacaat gggatcggtt catcaggctt aattattgat    300
ggctccgaag agcagaaaca gtattttttg ccacgtctgg caagtggtga aattattggt    360
tcattctgtt taactgaacc tgattccggt tcagatgctg cctctttaaa accacagcg     420 gtgaaagatg gtgatcatta catttttaat ggcactaagc gttacatcac caatgcaccg    480
catgcgggtg tctttactgt catggcacgt accagtaccg aaattaaagg tacaggtgga    540
atttcagcct ttatcgtgga cagtaaaact cctggtattt ccttgggtaa acgtgataag    600
aagatgggcc aaaaaggtgc acatacctgt gatgtgattt ttgaaaactg tcgtattcct    660
gcatctgcac tcattggtgg tgttgaaggt gtaggtttta aaactgcaat gaaggtactt    720
gataaaggcc gtattcatat tgctgcatta agtgtaggtg ctgctacgcg tatgctggaa    780
gattccctac aatatgccgt tgagcgcaaa cagtttggtc aagcgattgc gaacttccag    840
ttgattcaag gtatgttagc cgattctaaa gctgaaattt acgcagcaaa atgtatggta    900
ttagatgctg cccgacttcg tgatgctgga cagaatgtca gcacggaagc atcttgtgcc    960
aagatgtttg ccactgaaat gtgtggccgt gtcgcagatc gtggcgtaca gatccatggt   1020
ggtgcgggtt atatcagtga aatgctatt gagcgttttt accgtgatgt acgtttattc   1080
cgtttgtatg aaggtacaac gcaaatccaa caggtcatta ttgcccgcaa tatgatccgt   1140
gaagcgactc aataa                                                      1155

<210> SEQ ID NO 6
<211> LENGTH: 384
<212> TYPE: PRT
<213> ORGANISM: Acinetobacter sp.
```

```
<400> SEQUENCE: 6

Met Ile Arg Asp Gln Asp Thr Leu Asn Gln Leu Val Asp Met Ile Arg
  1               5                  10                  15

Gln Phe Val Asp Gly Val Leu Ile Pro Asn Glu Glu Ile Val Ala Glu
                 20                  25                  30

Thr Asp Glu Ile Pro Ala Glu Ile Val Gln Gln Met Lys Glu Leu Gly
             35                  40                  45

Leu Phe Gly Leu Thr Ile Pro Glu Glu Tyr Glu Gly Leu Gly Leu Thr
         50                  55                  60

Met Glu Glu Val Tyr Ile Ala Phe Glu Leu Gly Arg Thr Ser Pro
 65                  70                  75                  80

Ala Phe Arg Ser Leu Ile Gly Thr Asn Asn Gly Ile Gly Ser Ser Gly
                 85                  90                  95

Leu Ile Ile Asp Gly Ser Glu Glu Gln Lys Gln Tyr Phe Leu Pro Arg
            100                 105                 110

Leu Ala Ser Gly Glu Ile Ile Gly Ser Phe Cys Leu Thr Glu Pro Asp
        115                 120                 125

Ser Gly Ser Asp Ala Ala Ser Leu Lys Thr Thr Ala Val Lys Asp Gly
    130                 135                 140

Asp His Tyr Ile Leu Asn Gly Thr Lys Arg Tyr Ile Thr Asn Ala Pro
145                 150                 155                 160

His Ala Gly Val Phe Thr Val Met Ala Arg Thr Ser Thr Glu Ile Lys
                165                 170                 175

Gly Thr Gly Gly Ile Ser Ala Phe Ile Val Asp Ser Lys Thr Pro Gly
            180                 185                 190

Ile Ser Leu Gly Lys Arg Asp Lys Met Gly Gln Lys Gly Ala His
        195                 200                 205

Thr Cys Asp Val Ile Phe Glu Asn Cys Arg Ile Pro Ala Ser Ala Leu
    210                 215                 220

Ile Gly Gly Val Glu Gly Val Gly Phe Lys Thr Ala Met Lys Val Leu
225                 230                 235                 240

Asp Lys Gly Arg Ile His Ile Ala Ala Leu Ser Val Gly Ala Ala Thr
                245                 250                 255

Arg Met Leu Glu Asp Ser Leu Gln Tyr Ala Val Glu Arg Lys Gln Phe
            260                 265                 270

Gly Gln Ala Ile Ala Asn Phe Gln Leu Ile Gln Gly Met Leu Ala Asp
        275                 280                 285

Ser Lys Ala Glu Ile Tyr Ala Ala Lys Cys Met Val Leu Asp Ala Ala
    290                 295                 300

Arg Leu Arg Asp Ala Gly Gln Asn Val Ser Thr Glu Ala Ser Cys Ala
305                 310                 315                 320

Lys Met Phe Ala Thr Glu Met Cys Gly Arg Val Ala Asp Arg Gly Val
                325                 330                 335

Gln Ile His Gly Gly Ala Gly Tyr Ile Ser Glu Tyr Ala Ile Glu Arg
            340                 345                 350

Phe Tyr Arg Asp Val Arg Leu Phe Arg Leu Tyr Glu Gly Thr Thr Gln
        355                 360                 365

Ile Gln Gln Val Ile Ile Ala Arg Asn Met Ile Arg Glu Ala Thr Gln
    370                 375                 380

<210> SEQ ID NO 7
<211> LENGTH: 1719
<212> TYPE: DNA
<213> ORGANISM: Acinetobacter sp.
```

<400> SEQUENCE: 7

```
atgcaagaac aagaaatcga acgcgaatca atggagtttg acgtcgtgat tgtcggcgca      60
ggaccggccg gtctttctgc agcgatcaag atccgtcaac ttgcaattga aaacaacctg     120
aacgatctgt cggtttgtgt ggtggaaaaa ggctctgaag tcggtgcgca catcttgtcc     180
ggtgcggtac tggaaccacg tgccatgaat gagctgttcc cgaactggaa ggaagaaggt     240
gcacctttaa atgttccagt gaccgaagac aagacctatt cctgctctc ggatgaaaaa      300
tcacaagaag cgccacactg gatggtgcct aaaccatgc ataacgatgg caactatgtt      360
atctcgctcg gcaacgtagt gcgctggttg ggtcaaaaag cggaagagct ggaagtatct     420
attttcccgg gctttgccgc tgctgaaatt ctgtaccatg cagatggttc ggtgaaaggc     480
attcaaaccg gtgacatggg cattggcaag gatggcgaac cgacccataa ctttactccg     540
ggctatgaac tgcatgccaa atacaccctg tttgctgaag ctgccgtgg ccacctcggc      600
aagcgtttaa ttgccaaata caacctcgat aaagattcag atccacaaca ttacggtatc     660
ggtatcaaag agctgtggga atcgacccg gcgaaacaca agccaggtct ggtgatgcac      720
ggtgccggct ggccattgtc tgaaaccggt tcttcaggcg gctggtggtt gtatcatgcg     780
gaaaacaatc aggtgacttt gggcatgatc gtcgatctgt cttacaccaa cccgcatatg     840
tatccgttta tggaaatgca gcgctggaaa acccatccgc tgatcaagca gtatctggaa     900
ggtggcaaac gtatttctta tggcgcgcgt gcggtaacca aagcggctt taactcgcta      960
ccgaaattta ccttcccggg cggatcgctg attggtgacg atgccggctt cctgaacttt    1020
gccaaaatca agggctcaca taccgcgatg aaatccggca tgctctgcgg tgaagcagtg    1080
tttgaagcca ttgctgccgg tgtggaaaaa ggtggtgacc ttgcggttgc gcgtgtgacg    1140
gaaggcgaag acttgtttgc caaaaaactg acttcttaca ccgacaagtt caataatagc    1200
tggctgaaag aagagctgta caactcgcgt aactttggcc cggccatgca caagtttggt    1260
cagtggctcg gtggtgcgtt taactttatc gaccagaacg tgtttaaggt gccgtttacc    1320
ctgcatgacc tggtgacgga tttcggtgcg ctgaaaaccg tcgatgcggt gaacttcaag    1380
ccgaattatc aaaaccgga tggcaaactg accttgacc gtctgtcttc ggtgtttgta      1440
tccaacacgg tgcatgaaga aaaccagcca gcgcatttaa aactgactga cacttcgatt    1500
ccggtgaatg tcaacctgcc aaaatgggat gaaccggcgc agcgctactg ccccgcgggt    1560
gtatacgaaa tcatggaaaa tgatgacggt tcgaaacgct tccagatcaa tgcagccaac    1620
tgtgtgcact gcaagacctg tgacatcaag gatccttcac agaacatcac ctgggtaaca    1680
ccggaaggtg gtggtggtcc aaactatccg aatatgtaa                           1719
```

<210> SEQ ID NO 8
<211> LENGTH: 572
<212> TYPE: PRT
<213> ORGANISM: Acinetobacter sp.

<400> SEQUENCE: 8

```
Met Gln Glu Gln Glu Ile Glu Arg Glu Ser Met Glu Phe Asp Val Val
  1               5                  10                  15

Ile Val Gly Ala Gly Pro Ala Gly Leu Ser Ala Ala Ile Lys Ile Arg
             20                  25                  30

Gln Leu Ala Ile Glu Asn Asn Leu Asn Asp Leu Ser Val Cys Val Val
         35                  40                  45

Glu Lys Gly Ser Glu Val Gly Ala His Ile Leu Ser Gly Ala Val Leu
```

-continued

```
        50                  55                  60
Glu Pro Arg Ala Met Asn Glu Leu Phe Pro Asn Trp Lys Glu Gly
 65                  70                  75                  80
Ala Pro Leu Asn Val Pro Val Thr Glu Asp Lys Thr Tyr Phe Leu Leu
                 85                  90                  95
Ser Asp Glu Lys Ser Gln Glu Ala Pro His Trp Met Val Pro Lys Thr
                100                 105                 110
Met His Asn Asp Gly Asn Tyr Val Ile Ser Leu Gly Asn Val Val Arg
                115                 120                 125
Trp Leu Gly Gln Lys Ala Glu Leu Glu Val Ser Ile Phe Pro Gly
    130                 135                 140
Phe Ala Ala Ala Glu Ile Leu Tyr His Ala Asp Gly Ser Val Lys Gly
145                 150                 155                 160
Ile Gln Thr Gly Asp Met Gly Ile Gly Lys Asp Gly Glu Pro Thr His
                165                 170                 175
Asn Phe Thr Pro Gly Tyr Glu Leu His Ala Lys Tyr Thr Leu Phe Ala
                180                 185                 190
Glu Gly Cys Arg Gly His Leu Gly Lys Arg Leu Ile Ala Lys Tyr Asn
                195                 200                 205
Leu Asp Lys Asp Ser Asp Pro Gln His Tyr Gly Ile Gly Ile Lys Glu
    210                 215                 220
Leu Trp Glu Ile Asp Pro Ala Lys His Lys Pro Gly Leu Val Met His
225                 230                 235                 240
Gly Ala Gly Trp Pro Leu Ser Glu Thr Gly Ser Ser Gly Gly Trp Trp
                245                 250                 255
Leu Tyr His Ala Glu Asn Asn Gln Val Thr Leu Gly Met Ile Val Asp
                260                 265                 270
Leu Ser Tyr Thr Asn Pro His Met Tyr Pro Phe Met Glu Met Gln Arg
    275                 280                 285
Trp Lys Thr His Pro Leu Ile Lys Gln Tyr Leu Glu Gly Gly Lys Arg
    290                 295                 300
Ile Ser Tyr Gly Ala Arg Ala Val Thr Lys Gly Gly Phe Asn Ser Leu
305                 310                 315                 320
Pro Lys Phe Thr Phe Pro Gly Gly Ser Leu Ile Gly Asp Asp Ala Gly
                325                 330                 335
Phe Leu Asn Phe Ala Lys Ile Lys Gly Ser His Thr Ala Met Lys Ser
                340                 345                 350
Gly Met Leu Cys Gly Glu Ala Val Phe Glu Ala Ile Ala Ala Gly Val
    355                 360                 365
Glu Lys Gly Gly Asp Leu Ala Val Ala Arg Val Thr Glu Gly Glu Asp
    370                 375                 380
Leu Phe Ala Lys Lys Leu Thr Ser Tyr Thr Asp Lys Phe Asn Asn Ser
385                 390                 395                 400
Trp Leu Lys Glu Glu Leu Tyr Asn Ser Arg Asn Phe Gly Pro Ala Met
                405                 410                 415
His Lys Phe Gly Gln Trp Leu Gly Gly Ala Phe Asn Phe Ile Asp Gln
                420                 425                 430
Asn Val Phe Lys Val Pro Phe Thr Leu His Asp Leu Val Thr Asp Phe
                435                 440                 445
Gly Ala Leu Lys Thr Val Asp Ala Val Asn Phe Lys Pro Asn Tyr Pro
    450                 455                 460
Lys Pro Asp Gly Lys Leu Thr Phe Asp Arg Leu Ser Ser Val Phe Val
465                 470                 475                 480
```

```
Ser Asn Thr Val His Glu Glu Asn Gln Pro Ala His Leu Lys Leu Thr
                485                 490                 495

Asp Thr Ser Ile Pro Val Asn Val Asn Leu Pro Lys Trp Asp Glu Pro
            500                 505                 510

Ala Gln Arg Tyr Cys Pro Ala Gly Val Tyr Glu Ile Met Glu Asn Asp
        515                 520                 525

Asp Gly Ser Lys Arg Phe Gln Ile Asn Ala Ala Asn Cys Val His Cys
    530                 535                 540

Lys Thr Cys Asp Ile Lys Asp Pro Ser Gln Asn Ile Thr Trp Val Thr
545                 550                 555                 560

Pro Glu Gly Gly Gly Gly Pro Asn Tyr Pro Asn Met
                565                 570

<210> SEQ ID NO 9
<211> LENGTH: 1644
<212> TYPE: DNA
<213> ORGANISM: Acinetobacter sp.

<400> SEQUENCE: 9
```

| | | |
|---|---|---|
| atggagatta tcatgtcaca aaaaatggat tttgatgcta tcgtgattgg tggtggtttt | 60 |
| ggcggacttt atgcagtcaa aaaattaaga gacgagctcg aacttaaggt tcaggctttt | 120 |
| gataaagcca cggatgtcgc aggtacttgg tactggaacc gttacccagg tgcattgtcg | 180 |
| gatacagaaa cccacctcta ctgctattct tgggataaag aattactaca atcgctagaa | 240 |
| atcaagaaaa aatatgtgca aggccctgat gtacgcaagt atttacagca gtggctgaa | 300 |
| aagcatgatt taaagaagag ctatcaattc aataccgcgg ttcaatcggc tcattacaac | 360 |
| gaagcagatg ccttgtggga agtcaccact gaatatggtg ataagtacac ggcgcgtttc | 420 |
| ctcatcactg ctttaggctt attgtctgcg cctaacttgc caaacatcaa aggcattaat | 480 |
| cagtttaaag gtgagctgca tcataccagc cgctggccag atgacgtaag ttttgaaggt | 540 |
| aaacgtgtcg gcgtgattgg tacgggttcc accggtgttc aggttattac ggctgtggca | 600 |
| cctctggcta aacacctcac tgtcttccag cgttctgcac aatacagcgt tccaattggc | 660 |
| aatgatccac tgtctgaaga agatgttaaa aagatcaaag acaattatga caaaatttgg | 720 |
| gatggtgtat ggaattcagc ccttgccttt ggcctgaatg aaagcacagt gccagcaatg | 780 |
| agcgtatcag ctgaagaacg caaggcagtt tttgaaaagg catggcaaac aggtggcggt | 840 |
| ttccgtttca tgtttgaaac tttcggtgat attgccacca atatggaagc caatatcgaa | 900 |
| gcgcaaaatt tcattaaggg taaaattgct gaaatcgtca agatccagc cattgcacag | 960 |
| aagcttatgc cacaggattt gtatgcaaaa cgtccgttgt gtgacagtgg ttactacaac | 1020 |
| accctttaacc gtgacaatgt ccgtttagaa gatgtgaaag ccaatccgat tgttgaaatt | 1080 |
| accgaaaacg tgtgaaaact cgaaaatggc gatttcgttg aattagacat gctgatatgt | 1140 |
| gccacaggtt ttgatgccgt cgatggcaac tatgtgcgca tggacattca aggtaaaaac | 1200 |
| ggcttggcca tgaaagacta ctggaaagaa ggtccgtcga gctatatggg tgtcaccgta | 1260 |
| aataactatc aaacatgtt catggtgctt ggaccgaatg gcccgtttac caacctgccg | 1320 |
| ccatcaattg aatcacaggt ggaatggatc agtgatacca ttcaatacac ggttgaaaac | 1380 |
| aatgttgaat ccattgaagc gacaaaagaa gcggaagaac aatggactca acttgcgcc | 1440 |
| aatattgcgg aaatgacctt attccctaaa gcgcaatcct ggattttggg tgcgaatatc | 1500 |
| ccgggcaaga aaaacacggt ttacttctat ctcggtggtt taaaagaata tcgcagtgcg | 1560 |

```
ctagccaact gcaaaaacca tgcctatgaa ggttttgata ttcaattaca acgttcagat    1620
atcaagcaac ctgccaatgc ctaa                                           1644
```

<210> SEQ ID NO 10
<211> LENGTH: 547
<212> TYPE: PRT
<213> ORGANISM: Acinetobacter sp.

<400> SEQUENCE: 10

```
Met Glu Ile Ile Met Ser Gln Lys Met Asp Phe Asp Ala Ile Val Ile
  1               5                  10                  15

Gly Gly Gly Phe Gly Gly Leu Tyr Ala Val Lys Lys Leu Arg Asp Glu
                 20                  25                  30

Leu Glu Leu Lys Val Gln Ala Phe Asp Lys Ala Thr Asp Val Ala Gly
             35                  40                  45

Thr Trp Tyr Trp Asn Arg Tyr Pro Gly Ala Leu Ser Asp Thr Glu Thr
 50                  55                  60

His Leu Tyr Cys Tyr Ser Trp Asp Lys Glu Leu Leu Gln Ser Leu Glu
 65                  70                  75                  80

Ile Lys Lys Lys Tyr Val Gln Gly Pro Asp Val Arg Lys Tyr Leu Gln
                 85                  90                  95

Gln Val Ala Glu Lys His Asp Leu Lys Lys Ser Tyr Gln Phe Asn Thr
            100                 105                 110

Ala Val Gln Ser Ala His Tyr Asn Glu Ala Asp Ala Leu Trp Glu Val
        115                 120                 125

Thr Thr Glu Tyr Gly Asp Lys Tyr Thr Ala Arg Phe Leu Ile Thr Ala
130                 135                 140

Leu Gly Leu Leu Ser Ala Pro Asn Leu Pro Asn Ile Lys Gly Ile Asn
145                 150                 155                 160

Gln Phe Lys Gly Glu Leu His His Thr Ser Arg Trp Pro Asp Asp Val
                165                 170                 175

Ser Phe Glu Gly Lys Arg Val Gly Val Ile Gly Thr Gly Ser Thr Gly
            180                 185                 190

Val Gln Val Ile Thr Ala Val Ala Pro Leu Ala Lys His Leu Thr Val
        195                 200                 205

Phe Gln Arg Ser Ala Gln Tyr Ser Val Pro Ile Gly Asn Asp Pro Leu
210                 215                 220

Ser Glu Glu Asp Val Lys Lys Ile Lys Asp Asn Tyr Asp Lys Ile Trp
225                 230                 235                 240

Asp Gly Val Trp Asn Ser Ala Leu Ala Phe Gly Leu Asn Glu Ser Thr
                245                 250                 255

Val Pro Ala Met Ser Val Ser Ala Glu Glu Arg Lys Ala Val Phe Glu
            260                 265                 270

Lys Ala Trp Gln Thr Gly Gly Gly Phe Arg Phe Met Phe Glu Thr Phe
        275                 280                 285

Gly Asp Ile Ala Thr Asn Met Glu Ala Asn Ile Glu Ala Gln Asn Phe
290                 295                 300

Ile Lys Gly Lys Ile Ala Glu Ile Val Lys Asp Pro Ala Ile Ala Gln
305                 310                 315                 320

Lys Leu Met Pro Gln Asp Leu Tyr Ala Lys Arg Pro Leu Cys Asp Ser
                325                 330                 335

Gly Tyr Tyr Asn Thr Phe Asn Arg Asp Asn Val Arg Leu Glu Asp Val
            340                 345                 350

Lys Ala Asn Pro Ile Val Glu Ile Thr Glu Asn Gly Val Lys Leu Glu
```

```
                355                 360                 365
Asn Gly Asp Phe Val Glu Leu Asp Met Leu Ile Cys Ala Thr Gly Phe
            370                 375                 380
Asp Ala Val Asp Gly Asn Tyr Val Arg Met Asp Ile Gln Gly Lys Asn
385                 390                 395                 400
Gly Leu Ala Met Lys Asp Tyr Trp Lys Glu Gly Pro Ser Ser Tyr Met
                405                 410                 415
Gly Val Thr Val Asn Asn Tyr Pro Asn Met Phe Met Val Leu Gly Pro
            420                 425                 430
Asn Gly Pro Phe Thr Asn Leu Pro Pro Ser Ile Glu Ser Gln Val Glu
                435                 440                 445
Trp Ile Ser Asp Thr Ile Gln Tyr Thr Val Glu Asn Asn Val Glu Ser
            450                 455                 460
Ile Glu Ala Thr Lys Glu Ala Glu Glu Gln Trp Thr Gln Thr Cys Ala
465                 470                 475                 480
Asn Ile Ala Glu Met Thr Leu Phe Pro Lys Ala Gln Ser Trp Ile Phe
                485                 490                 495
Gly Ala Asn Ile Pro Gly Lys Lys Asn Thr Val Tyr Phe Tyr Leu Gly
                500                 505                 510
Gly Leu Lys Glu Tyr Arg Ser Ala Leu Ala Asn Cys Lys Asn His Ala
            515                 520                 525
Tyr Glu Gly Phe Asp Ile Gln Leu Gln Arg Ser Asp Ile Lys Gln Pro
            530                 535                 540
Ala Asn Ala
545

<210> SEQ ID NO 11
<211> LENGTH: 1497
<212> TYPE: DNA
<213> ORGANISM: Acinetobacter sp.

<400> SEQUENCE: 11 atgggggca tccccatat tccattttgt ttaacatcag tcatatgcca gggatgtctt      60
atcatgaact atccaaatat acctttatat atcaacggtg agtttctaga tcataccaat    120
agagacgtca aagaagtttt taatccagtg aaccatgaat gtattggact catggcctgt    180
gcatcacaag cagacctgga ctacgcactt gaaagttcac aacaggcttt tctaaggtgg    240
aaaaaaactt ctcctatcac ccgtagtgaa atcctcagaa cctttgcgaa actagcgcgt    300
gaaaaagcag cagaaatcgg gcgcaatatt accccttgatc aaggtaagcc cctgaaagaa    360
gccattgcag aagtcactgt ctgtgcagaa catgcagaat ggcatgcaga agaatgccga    420
cgcatttatg gccgtgttat tccaccgcgt aacccaaatg tacagcaact agtagtcaga    480
gaaccgctgg gcgtatgtct ggcattttca ccgtggaatt cccgtttaa tcaggcaatt    540 cgtaaaattt ctgctgcaat gctgccggc tgcaccatca ttgtgaaagg ttctggcgac    600
acaccaagcg cggtatatgc gattgcccag ctatttcatg aggcgggttt gccgaatggt    660
gtgctgaatg tgatttgggg tgactcaaac ttcatttctg attacatgat caaatcgccg    720
atcatccaaa agatttcatt cacaggctca accccgtgg gtaaaaaatt agcctcgcaa    780
gcgagtctgt atatgaagcc ttgcaccatg gaattgggtg gtcatgcacc ggtcatcgtc    840
tgtgatgatg ctgatattga tgccgctgtt gaacatctgg tcggttataa attccgtaat    900
gcaggacagg tctgtgtatc accaacccgt ttttatgtgc aggaaggtat ttataaggaa    960
ttttctgaga aagtggtgtt aagagccaaa cagatcaaag tgggttgtgg cttagacgca   1020
```

```
tcctcagata tgggaccatt ggctcaagct cgccgcatgc atgcaatgca acaaattgtt   1080
gaagatgcgg ttcataaagg ctcaaaatta ctgcttggcg aaataaaat ttctgacaaa   1140 ggcaatttt  tgaaccaac ggtactcggt gacttgtgca atgacaccca gtttatgaat   1200
gacgagccat ttggtccgat cattggtttg ataccttttg acacaataga ccatgtcctg   1260
gaagaagcaa atcgattacc atttggatta gcctcttacg cttttaccac atccagcaaa   1320
aatgcgcatc aaatctcata cggactggag gctggcatgg tttcgattaa ccacatggga   1380
ttggcgctcg ctgaaacacc ttttggtggt attaaggata gcggttttgg tagtgaaggg   1440
ggtatcgaaa cctttgacgg ttacctcaga accaaattta ttacgcaact caattag      1497
```

<210> SEQ ID NO 12
<211> LENGTH: 498
<212> TYPE: PRT
<213> ORGANISM: Acinetobacter sp.

<400> SEQUENCE: 12

```
Met Gly Gly Ile Pro His Ile Pro Phe Cys Leu Thr Ser Val Ile Cys
 1               5                  10                  15

Gln Gly Cys Leu Ile Met Asn Tyr Pro Asn Ile Pro Leu Tyr Ile Asn
            20                  25                  30

Gly Glu Phe Leu Asp His Thr Asn Arg Asp Val Lys Glu Val Phe Asn
        35                  40                  45

Pro Val Asn His Glu Cys Ile Gly Leu Met Ala Cys Ala Ser Gln Ala
    50                  55                  60

Asp Leu Asp Tyr Ala Leu Glu Ser Ser Gln Gln Ala Phe Leu Arg Trp
65                  70                  75                  80

Lys Lys Thr Ser Pro Ile Thr Arg Ser Glu Ile Leu Arg Thr Phe Ala
                85                  90                  95

Lys Leu Ala Arg Glu Lys Ala Ala Glu Ile Gly Arg Asn Ile Thr Leu
            100                 105                 110

Asp Gln Gly Lys Pro Leu Lys Glu Ala Ile Ala Glu Val Thr Val Cys
        115                 120                 125

Ala Glu His Ala Glu Trp His Ala Glu Glu Cys Arg Arg Ile Tyr Gly
    130                 135                 140

Arg Val Ile Pro Pro Arg Asn Pro Asn Val Gln Gln Leu Val Val Arg
145                 150                 155                 160

Glu Pro Leu Gly Val Cys Leu Ala Phe Ser Pro Trp Asn Phe Pro Phe
                165                 170                 175

Asn Gln Ala Ile Arg Lys Ile Ser Ala Ala Ile Ala Ala Gly Cys Thr
            180                 185                 190

Ile Ile Val Lys Gly Ser Gly Asp Thr Pro Ser Ala Val Tyr Ala Ile
        195                 200                 205

Ala Gln Leu Phe His Glu Ala Gly Leu Pro Asn Gly Val Leu Asn Val
    210                 215                 220

Ile Trp Gly Asp Ser Asn Phe Ile Ser Asp Tyr Met Ile Lys Ser Pro
225                 230                 235                 240

Ile Ile Gln Lys Ile Ser Phe Thr Gly Ser Thr Pro Val Gly Lys Lys
                245                 250                 255

Leu Ala Ser Gln Ala Ser Leu Tyr Met Lys Pro Cys Thr Met Glu Leu
            260                 265                 270

Gly Gly His Ala Pro Val Ile Val Cys Asp Asp Ala Asp Ile Asp Ala
        275                 280                 285
```

Ala Val Glu His Leu Val Gly Tyr Lys Phe Arg Asn Ala Gly Gln Val
            290                 295                 300

Cys Val Ser Pro Thr Arg Phe Tyr Val Gln Glu Gly Ile Tyr Lys Glu
305                 310                 315                 320

Phe Ser Glu Lys Val Val Leu Arg Ala Lys Gln Ile Lys Val Gly Cys
                325                 330                 335

Gly Leu Asp Ala Ser Ser Asp Met Gly Pro Leu Ala Gln Ala Arg Arg
            340                 345                 350

Met His Ala Met Gln Gln Ile Val Glu Asp Ala Val His Lys Gly Ser
            355                 360                 365

Lys Leu Leu Gly Gly Asn Lys Ile Ser Asp Lys Gly Asn Phe Phe
            370                 375                 380

Glu Pro Thr Val Leu Gly Asp Leu Cys Asn Asp Thr Gln Phe Met Asn
385                 390                 395                 400

Asp Glu Pro Phe Gly Pro Ile Ile Gly Leu Ile Pro Phe Asp Thr Ile
                405                 410                 415

Asp His Val Leu Glu Glu Ala Asn Arg Leu Pro Phe Gly Leu Ala Ser
            420                 425                 430

Tyr Ala Phe Thr Thr Ser Ser Lys Asn Ala His Gln Ile Ser Tyr Gly
            435                 440                 445

Leu Glu Ala Gly Met Val Ser Ile Asn His Met Gly Leu Ala Leu Ala
            450                 455                 460

Glu Thr Pro Phe Gly Gly Ile Lys Asp Ser Gly Phe Gly Ser Glu Gly
465                 470                 475                 480

Gly Ile Glu Thr Phe Asp Gly Tyr Leu Arg Thr Lys Phe Ile Thr Gln
                485                 490                 495

Leu Asn

<210> SEQ ID NO 13
<211> LENGTH: 942
<212> TYPE: DNA
<213> ORGANISM: Acinetobacter sp.

<400> SEQUENCE: 13

| | | | | | |
|---|---|---|---|---|---|
| atgagcacag | acaaagcaaa | tacgctgatc | aaacccgaag | atgtcgtgtt | atggattccg | 60 |
| ggtaatgtca | caattgacag | catgaatgcc | ggttgggaaa | acattgcaat | cagagggtac | 120 |
| gaatatacca | acctcgatgt | gcatattcct | gccatgcgtg | actacatgat | cgtcaactat | 180 |
| aaaaaaagtg | cggcggaaat | gcgtagaaaa | ggcgatgcct | cttgggatac | ccaagtggtt | 240 |
| aagccgggtt | atgtctcctt | gttgacctgt | ggtgaagatt | cccgctgggc | gtggaatgac | 300 |
| catattgccg | tcacccatgt | ctacatttcg | catgactcca | tcacctcaat | ggcgaataag | 360 |
| gtgtttgatt | atgatatcgc | ttcgatccga | atcagagacg | aagtcggtgt | ggaagatcat | 420 |
| gttttacctg | ctctgacttc | acttttagaa | ctagaattaa | agcaaggtgg | tttaggtgga | 480 |
| aacctgtatt | tagagagcat | taaaaccag | atcgccctgc | atttactccg | tcagtatgcc | 540 |
| aaattagatt | ttaaggaagg | acagtgccgt | tctggtttta | ctcccctaca | acgcagactg | 600 |
| ttattagaat | ttatcaatga | aaacatgagc | attaaaatta | ccctcgaaga | tttagcggga | 660 |
| ttagtcaaga | tgagcgtgcc | tcatttaatg | agaaaattta | aagtcgattt | tggtaattcc | 720 |
| cctgctgcct | acatcatgaa | tctcagggtg | caatttgcta | aacgtttgct | cacttcaaaa | 780 |
| aaagaaattc | cactgaaagt | gattgccagt | gaagccggtt | tttgcgatca | gagccatatg | 840 |
| acccgagtat | ttcaaaaatt | ttttgggaaa | acacccatcg | aaatcagaca | ggaacacacc | 900 |

```
aatctcgtgt ctgaaaattc agtctcctct attgtttttt ga                        942
```

<210> SEQ ID NO 14
<211> LENGTH: 313
<212> TYPE: PRT
<213> ORGANISM: Acinetobacter sp.

<400> SEQUENCE: 14

```
Met Ser Thr Asp Lys Ala Asn Thr Leu Ile Lys Pro Glu Asp Val Val
 1               5                  10                  15

Leu Trp Ile Pro Gly Asn Val Thr Ile Asp Ser Met Asn Ala Gly Trp
            20                  25                  30

Glu Asn Ile Ala Ile Arg Gly Tyr Glu Tyr Thr Asn Leu Asp Val His
        35                  40                  45

Ile Pro Ala Met Arg Asp Tyr Met Ile Val Asn Tyr Lys Lys Ser Ala
    50                  55                  60

Ala Glu Met Arg Arg Lys Gly Asp Ala Ser Trp Asp Thr Gln Val Val
65                  70                  75                  80

Lys Pro Gly Tyr Val Ser Leu Leu Thr Cys Gly Glu Asp Ser Arg Trp
                85                  90                  95

Ala Trp Asn Asp His Ile Ala Val Thr His Val Tyr Ile Ser His Asp
            100                 105                 110

Ser Ile Thr Ser Met Ala Asn Lys Val Phe Asp Tyr Asp Ile Ala Ser
        115                 120                 125

Ile Arg Ile Arg Asp Glu Val Gly Val Glu Asp His Val Leu Pro Ala
    130                 135                 140

Leu Thr Ser Leu Leu Glu Leu Glu Leu Lys Gln Gly Gly Leu Gly Gly
145                 150                 155                 160

Asn Leu Tyr Leu Glu Ser Ile Lys Asn Gln Ile Ala Leu His Leu Leu
                165                 170                 175

Arg Gln Tyr Ala Lys Leu Asp Phe Lys Glu Gly Gln Cys Arg Ser Gly
            180                 185                 190

Phe Thr Pro Leu Gln Arg Arg Leu Leu Glu Phe Ile Asn Glu Asn
        195                 200                 205

Met Ser Ile Lys Ile Thr Leu Glu Asp Leu Ala Gly Leu Val Lys Met
    210                 215                 220

Ser Val Pro His Leu Met Arg Lys Phe Lys Val Asp Phe Gly Asn Ser
225                 230                 235                 240

Pro Ala Ala Tyr Ile Met Asn Leu Arg Val Gln Phe Ala Lys Arg Leu
                245                 250                 255

Leu Thr Ser Lys Lys Glu Ile Pro Leu Lys Val Ile Ala Ser Glu Ala
            260                 265                 270

Gly Phe Cys Asp Gln Ser His Met Thr Arg Val Phe Gln Lys Phe Phe
        275                 280                 285

Gly Lys Thr Pro Ile Glu Ile Arg Gln Glu His Thr Asn Leu Val Ser
    290                 295                 300

Glu Asn Ser Val Ser Ser Ile Val Phe
305                 310
```

<210> SEQ ID NO 15
<211> LENGTH: 660
<212> TYPE: DNA
<213> ORGANISM: Acinetobacter sp.

<400> SEQUENCE: 15

```
gtgcgctcta tctggcttag acacaatctt gagaatttca aaaagcgatt aaaggcactt    60
```

```
gaaattaaag ttgctcaaga aggcattcag ttgaatgatc agcagattgc cgcattagaa    120
cgtaaacatg aagatgatgt tgcttgtggt gaaattgaaa cacatcatcc aggttacctt    180
ggagcacaag atactttta tgtcggaaat ctaaaaggtg ttgggcatat ttatcagcaa     240
acttttattg atacttatag caaagtggtt cactgcaagc tgtacacaac caagacacca    300
atcacagccg cagatttatt gaatgaccgc gtgttaccat tctatgagtc acaaggattg    360
ccaatgcttc gcattttgac cgacagaggc accgaatatt gcggtaaagt tgaacatcac    420
gattatgagc tttatttggc tctgaatgat attgatcaca ctaaaactaa agcagcatca    480
ccacaaacaa atgggatctg tgagcgcttc cataagacga tcttgcagga gttttatcag    540
attacttttc gaaagaaact ctatagctca ttagaagagt tacagcttga tctagacggt    600
tggctgaaat tctataatac tgaacgaacc catcagggta aggtgtgtaa tggcagatga    660
```

<210> SEQ ID NO 16
<211> LENGTH: 219
<212> TYPE: PRT
<213> ORGANISM: Acinetobacter sp.

<400> SEQUENCE: 16

```
Met Arg Ser Ile Trp Leu Arg His Asn Leu Glu Asn Phe Lys Lys Arg
  1               5                  10                  15

Leu Lys Ala Leu Glu Ile Lys Val Ala Gln Glu Gly Ile Gln Leu Asn
             20                  25                  30

Asp Gln Gln Ile Ala Ala Leu Glu Arg Lys His Glu Asp Asp Val Ala
         35                  40                  45

Cys Gly Glu Ile Glu Thr His His Pro Gly Tyr Leu Gly Ala Gln Asp
     50                  55                  60

Thr Phe Tyr Val Gly Asn Leu Lys Gly Val Gly His Ile Tyr Gln Gln
 65                  70                  75                  80

Thr Phe Ile Asp Thr Tyr Ser Lys Val Val His Cys Lys Leu Tyr Thr
                 85                  90                  95

Thr Lys Thr Pro Ile Thr Ala Ala Asp Leu Leu Asn Asp Arg Val Leu
            100                 105                 110

Pro Phe Tyr Glu Ser Gln Gly Leu Pro Met Leu Arg Ile Leu Thr Asp
        115                 120                 125

Arg Gly Thr Glu Tyr Cys Gly Lys Val Glu His His Asp Tyr Glu Leu
    130                 135                 140

Tyr Leu Ala Leu Asn Asp Ile Asp His Thr Lys Thr Lys Ala Ala Ser
145                 150                 155                 160

Pro Gln Thr Asn Gly Ile Cys Glu Arg Phe His Lys Thr Ile Leu Gln
                165                 170                 175

Glu Phe Tyr Gln Ile Thr Phe Arg Lys Lys Leu Tyr Ser Ser Leu Glu
            180                 185                 190

Glu Leu Gln Leu Asp Leu Asp Gly Trp Leu Lys Phe Tyr Asn Thr Glu
        195                 200                 205

Arg Thr His Gln Gly Lys Val Cys Asn Gly Arg
    210                 215
```

<210> SEQ ID NO 17
<211> LENGTH: 975
<212> TYPE: DNA
<213> ORGANISM: Acinetobacter sp.

<400> SEQUENCE: 17

-continued

```
atgttttatc ttggtattga tgttgctaaa gctaaaattg attgctgttt aattttagaa      60
aattctgcaa ataaaaagaa aaccaaaact ttttcaaata caccaaaagg ttttgagcaa     120
cttcaaacct ggctaaagca gcatgctgca acttctacgc agaccattat tttaatggaa     180
gcaacatcta tttatcatga actcttggtt aaatatttat ttgatgcggg ctatcaagtc     240
tgtgtaacca atcctgccag agctcgatat tttgctcaga gtatgtctaa gctgaataaa     300
acagacaagg tggatagtga ggtcctagct cgatttgcga tgactgccga tctacatttt     360
tggcaacctt tacctaaaca tattcaattg ctgaatgctt tgctggatag aagagctatt     420
ctttgtgaag atttacaacg tgaaaagaat cgtttggaaa aagcagagtc gaccttcacg     480
atggaacctg tacttcagtc tatccacaag agtattgaac agttaaacaa acacattcag     540
ggtatcgacc agcaaattga tgatcacatt aatcagaatc ctgatttaaa aaatgataaa     600
gaactgctca gcagtattcc agccattgca gatcgaacca gtttattaat gctcagtttc     660
ttgcgcagcc atacttttga aagggctagt caagcggctg cctttgtcgg tttggtcccc     720
attcaaaagc aatcgggtag ttccattcat ggcagaagcc gtttatccaa agcgggctct     780
tccaaaatac gtgctggttt atatatggca gccattgtcg caactcggca taaccctcac     840
atcagggcaa tgaatgaacg tttattggcg aatggtaaaa ccaagatgat agcgattgga     900
gccgcgatga ggaagttgat tcatctttgt tatggtgtgc tcaaacacca acagccttat     960
caagcagatt attga                                                      975
```

<210> SEQ ID NO 18
<211> LENGTH: 324
<212> TYPE: PRT
<213> ORGANISM: Acinetobacter sp.

<400> SEQUENCE: 18

```
Met Phe Tyr Leu Gly Ile Asp Val Ala Lys Ala Lys Ile Asp Cys Cys
 1               5                  10                  15

Leu Ile Leu Glu Asn Ser Ala Asn Lys Lys Thr Lys Thr Phe Ser
            20                  25                  30

Asn Thr Pro Lys Gly Phe Glu Gln Leu Gln Thr Trp Leu Lys Gln His
        35                  40                  45

Ala Ala Thr Ser Thr Gln Thr Ile Ile Leu Met Glu Ala Thr Ser Ile
    50                  55                  60

Tyr His Glu Leu Leu Val Lys Tyr Leu Phe Asp Ala Gly Tyr Gln Val
65                  70                  75                  80

Cys Val Thr Asn Pro Ala Arg Ala Arg Tyr Phe Ala Gln Ser Met Ser
                85                  90                  95

Lys Leu Asn Lys Thr Asp Lys Val Asp Ser Glu Val Leu Ala Arg Phe
            100                 105                 110

Ala Met Thr Ala Asp Leu His Phe Trp Gln Pro Leu Pro Lys His Ile
        115                 120                 125

Gln Leu Leu Asn Ala Leu Leu Asp Arg Arg Ala Ile Leu Cys Glu Asp
    130                 135                 140

Leu Gln Arg Glu Lys Asn Arg Leu Glu Lys Ala Glu Ser Thr Phe Thr
145                 150                 155                 160

Met Glu Pro Val Leu Gln Ser Ile His Lys Ser Ile Glu Gln Leu Asn
                165                 170                 175

Lys His Ile Gln Gly Ile Asp Gln Gln Ile Asp Asp His Ile Asn Gln
            180                 185                 190

Asn Pro Asp Leu Lys Asn Asp Lys Glu Leu Leu Ser Ser Ile Pro Ala
```

```
          195                 200                      205
Ile Ala Asp Arg Thr Ser Leu Leu Met Leu Ser Phe Leu Arg Ser His
    210                 215                 220

Thr Phe Glu Arg Ala Ser Gln Ala Ala Ala Phe Val Gly Leu Val Pro
225                 230                 235                 240

Ile Gln Lys Gln Ser Gly Ser Ser Ile His Gly Arg Ser Arg Leu Ser
                245                 250                 255

Lys Ala Gly Ser Ser Lys Ile Arg Ala Gly Leu Tyr Met Ala Ala Ile
            260                 265                 270

Val Ala Thr Arg His Asn Pro His Ile Arg Ala Met Asn Glu Arg Leu
        275                 280                 285

Leu Ala Asn Gly Lys Thr Lys Met Ile Ala Ile Gly Ala Ala Met Arg
    290                 295                 300

Lys Leu Ile His Leu Cys Tyr Gly Val Leu Lys His Gln Gln Pro Tyr
305                 310                 315                 320

Gln Ala Asp Tyr
```

<210> SEQ ID NO 19
<211> LENGTH: 756
<212> TYPE: DNA
<213> ORGANISM: Acinetobacter sp.

<400> SEQUENCE: 19

```
atggaaaaaa ttatgtcaaa taaattcaac aataaagtcg ctttaattac tggcgctggt    60
tcaggtattg gtaaaagcac cgcactgctt ttggctcaac agggtgtaag tgtagtggtt   120
tcagatatta acctggaagc agcacagaaa gttgtggacg aaattgtcgc tttaggcggg   180
aaagcggctg cgaataaggc caatactgct gagcctgaag acatgaaagc tgcagtcgag   240
tttgcggtca gcacttttgg tgcactgcat ttggccttca ataatgcggg aattctgggt   300
gaagttaact ccaccgaaga attgagcatt gaaggatggc gtcgtgtgat tgatgtgaac   360
ttgaatgcgg ttttctacag catgcattat gaagttcctg caatcttggc cgcaggggc    420
ggagcgattg tcaataccgc ttctattgca ggcttgatcg ggattcaaaa tatttcaggc   480
tatgtcgctg caaaacatgg cgtaacgggt ctaacgaaag cggcggcatt ggaatatgca   540
gataaaggga ttcgcattaa ttcagtacat cctggctata tcaaaacgcc tttgattgca   600
gaatttgaag aagcagaaat ggtaaaacta catccgattg gtcgtttggg acagccggaa   660
gaagttgctc aggttgttgc cttcctactt tctgatgatg cttcatttgt gaccggtagt   720
cagtatgtgg tcgatggtgc atatacctcg aaataa                              756
```

<210> SEQ ID NO 20
<211> LENGTH: 251
<212> TYPE: PRT
<213> ORGANISM: Acinetobacter sp.

<400> SEQUENCE: 20

```
Met Glu Lys Ile Met Ser Asn Lys Phe Asn Asn Lys Val Ala Leu Ile
1               5                   10                  15

Thr Gly Ala Gly Ser Gly Ile Gly Lys Ser Thr Ala Leu Leu Leu Ala
            20                  25                  30

Gln Gln Gly Val Ser Val Val Ser Asp Ile Asn Leu Glu Ala Ala
        35                  40                  45

Gln Lys Val Val Asp Glu Ile Val Ala Leu Gly Gly Lys Ala Ala Ala
    50                  55                  60
```

```
Asn Lys Ala Asn Thr Ala Glu Pro Glu Asp Met Lys Ala Ala Val Glu
 65                  70                  75                  80

Phe Ala Val Ser Thr Phe Gly Ala Leu His Leu Ala Phe Asn Asn Ala
                 85                  90                  95

Gly Ile Leu Gly Glu Val Asn Ser Thr Glu Glu Leu Ser Ile Glu Gly
            100                 105                 110

Trp Arg Val Ile Asp Val Asn Leu Asn Ala Val Phe Tyr Ser Met
        115                 120                 125

His Tyr Glu Val Pro Ala Ile Leu Ala Ala Gly Gly Ala Ile Val
    130                 135                 140

Asn Thr Ala Ser Ile Ala Gly Leu Ile Gly Ile Gln Asn Ile Ser Gly
145                 150                 155                 160

Tyr Val Ala Ala Lys His Gly Val Thr Gly Leu Thr Lys Ala Ala Ala
                165                 170                 175

Leu Glu Tyr Ala Asp Lys Gly Ile Arg Ile Asn Ser Val His Pro Gly
            180                 185                 190

Tyr Ile Lys Thr Pro Leu Ile Ala Glu Phe Glu Glu Ala Glu Met Val
        195                 200                 205

Lys Leu His Pro Ile Gly Arg Leu Gly Gln Pro Glu Glu Val Ala Gln
    210                 215                 220

Val Val Ala Phe Leu Leu Ser Asp Asp Ala Ser Phe Val Thr Gly Ser
225                 230                 235                 240

Gln Tyr Val Val Asp Gly Ala Tyr Thr Ser Lys
                245                 250

<210> SEQ ID NO 21
<211> LENGTH: 900
<212> TYPE: DNA
<213> ORGANISM: Acinetobacter sp.

<400> SEQUENCE: 21
atgagtcaaa caacggaga gttaaaaatg aaacaaatga aaaactatttt ctatcatcgt      60 tcaaatcaaa aaatagctgc tttggtctttt gctttaactg ccgctttgga cctgcaagcc    120 gcagggggtga gttctgatgc cggggattat caagcacttc caggggggaac caacttagcg   180 gttgcctatt accagcatac ggaagcggat aaggcgtatg caaatggtga taaagtcgct   240
gatgatctcg atttaagcat tgatttggga atattgcgtt acgttcgttt tattgaagta   300 gggggattgga ttgtagatcc tcaattcctc ttgccttttg ccaagcaaaa gatgaatggc   360
gctgatgata tctcgggtgt cggtgattta attgtgggtg gtatcgcctg gccattgcat   420
gatgctgaaa agggcgcta ttttggttttc ggtggttttt tgaccgtacc taccggcagt   480
aatgaaacga agggttttgc catcagtaat gatcgctatc aatataatgt tcaggccggt   540
tattaccatg ctttaactga taaatttgcg cttgaggggg tggggcagtt tgaactttat   600
agcgagcaaa aatataccaa cattgagaaa gaggtttttt tccagacaga tttctccgca   660
ctctataaag tgaccgataa atccaatttg gctgtcacct ggagacatac cgatggcggt   720
aaagaaaagg tgaatggtgt cactgaacgt ggcagtgata gaaagataca ctttgtcgtt   780
tctgcttcta ccaatatcaa gccgaatctg cagctatatt acaatggcg acaagatgtg   840 aatgttgaaa atggcttgga aatttctgga cttcagtcac gtttactgta tgccttctaa   900

<210> SEQ ID NO 22
<211> LENGTH: 299
<212> TYPE: PRT
<213> ORGANISM: Acinetobacter sp.
```

<400> SEQUENCE: 22

| | | | | | | | | | | | | | | |
|---|---|---|---|---|---|---|---|---|---|---|---|---|---|---|
|Met|Ser|Gln|Asn|Asn|Gly|Glu|Leu|Lys|Met|Lys|Gln|Met|Lys|Asn|Tyr|
|1| | | |5| | | | |10| | | | |15| |

Phe Tyr His Arg Ser Asn Gln Lys Ile Ala Ala Leu Val Phe Ala Leu
             20              25             30

Thr Ala Ala Leu Asp Leu Gln Ala Ala Gly Val Ser Ser Asp Ala Gly
        35                40                45

Asp Tyr Gln Ala Leu Pro Gly Gly Thr Asn Leu Ala Val Ala Tyr Tyr
     50                 55              60

Gln His Thr Glu Ala Asp Lys Ala Tyr Ala Asn Gly Asp Lys Val Ala
65               70              75             80

Asp Asp Leu Asp Leu Ser Ile Asp Leu Gly Ile Leu Arg Tyr Val Arg
           85              90              95

Phe Ile Glu Val Gly Asp Trp Ile Val Asp Pro Gln Phe Leu Leu Pro
        100              105            110

Phe Ala Lys Gln Lys Met Asn Gly Ala Asp Asp Ile Ser Gly Val Gly
     115               120              125

Asp Leu Ile Val Gly Gly Ile Ala Trp Pro Leu His Asp Ala Glu Lys
    130               135              140

Gly Arg Tyr Phe Gly Phe Gly Gly Phe Leu Thr Val Pro Thr Gly Ser
145             150              155            160

Asn Glu Thr Lys Gly Phe Ala Ile Ser Asn Asp Arg Tyr Gln Tyr Asn
        165              170            175

Val Gln Ala Gly Tyr Tyr His Ala Leu Thr Asp Lys Phe Ala Leu Glu
          180              185            190

Gly Val Gly Gln Phe Glu Leu Tyr Ser Glu Gln Lys Tyr Thr Asn Ile
     195               200              205

Glu Lys Glu Val Phe Phe Gln Thr Asp Phe Ser Ala Leu Tyr Lys Val
    210               215              220

Thr Asp Lys Ser Asn Leu Ala Val Thr Trp Arg His Thr Asp Gly Gly
225              230             235            240

Lys Glu Lys Val Asn Gly Val Thr Glu Arg Gly Ser Asp Arg Lys Asp
        245              250            255

Thr Phe Val Val Ser Ala Ser Thr Asn Ile Lys Pro Asn Leu Gln Leu
          260              265            270

Leu Leu Gln Trp Arg Gln Asp Val Asn Val Glu Asn Gly Leu Glu Ile
     275               280              285

Ser Gly Leu Gln Ser Arg Leu Leu Tyr Ala Phe
    290               295

<210> SEQ ID NO 23
<211> LENGTH: 1059
<212> TYPE: DNA
<213> ORGANISM: Acinetobacter sp.

<400> SEQUENCE: 23

| | |
|---|---|
|atgcactgtt actgcgtgac gcatcatgga caaccactcg aagacgttga gaaagaaatt|60|
|ccgcaaccga aggtactga agttttactc catgtaaaag ccgcaggtct atgccatacg|120|
|gatttacact tatgggaagg ttattatgat ctaggtgggg gcaagcgttt atcccttgca|180|
|gatcgtgggc tgaagccacc cttaaccta agtcatgaaa ttacaggtca ggtggttgct|240|
|gtcggtccag atgcggaatc agtcaaggtc ggcatggtca gcttggttca tccatggatt|300|
|ggttgcggtg aatgcaacta ctgtaaacgt ggcgaagaaa acctgtgtgc caaaccgcaa|360|

```
cagttaggca tcgccaagcc gggtggtttt gccgaatata tcatcgtgcc gcatccacga      420
tatctggtgg atattgcagg tctggatctg gctgaagctg cacctttggc atgtgcaggc      480
gtgacaacat acagtgcact gaaaaaattc ggtgatttga ttcaaagcga gccggtggtg      540
atcattggtg ccggtggttt agggctgatg gcactcgagt tgctcaaagc tatgcaagcc      600
aaaggcgcaa tcgtagttga tattgatgac agcaaactgg aagcagcacg tgctgccggt      660
gcattatcgg tcatcaatag ccgaagtgag gatgctgctc aacagctgat tcaggcaact      720
gacggtggtg cacgtctgat ccttgatctg gttggcagta atccaacatt gagccttgcc      780
ttggcgagtg ctgcacgtgg tgggcatatt gtgatctgcg gattgatggg gggagaaatt      840
aagctttcca ttccggtgat tccaatgaga ccactcacaa tccagggcag ttatgtaggg      900
acggtagagg aattaagaga gctggtggag ctggtgaaag aaacccacat gtcagccatt      960
cccgtgaaaa aactgccaat ttcgcagatc aattccgcat ttggagactt gaaagatggc     1020
aacgtcatcg ggcgtattgt gcttatgcac gaaaactga                            1059
```

<210> SEQ ID NO 24
<211> LENGTH: 352
<212> TYPE: PRT
<213> ORGANISM: Acinetobacter sp.

<400> SEQUENCE: 24

```
Met His Cys Tyr Cys Val Thr His His Gly Gln Pro Leu Glu Asp Val
 1               5                  10                  15

Glu Lys Glu Ile Pro Gln Pro Lys Gly Thr Glu Val Leu Leu His Val
             20                  25                  30

Lys Ala Ala Gly Leu Cys His Thr Asp Leu His Leu Trp Glu Gly Tyr
         35                  40                  45

Tyr Asp Leu Gly Gly Gly Lys Arg Leu Ser Leu Ala Asp Arg Gly Leu
     50                  55                  60

Lys Pro Pro Leu Thr Leu Ser His Glu Ile Thr Gly Gln Val Val Ala
 65                  70                  75                  80

Val Gly Pro Asp Ala Glu Ser Val Lys Val Gly Met Val Ser Leu Val
                 85                  90                  95

His Pro Trp Ile Gly Cys Gly Glu Cys Asn Tyr Cys Lys Arg Gly Glu
            100                 105                 110

Glu Asn Leu Cys Ala Lys Pro Gln Gln Leu Gly Ile Ala Lys Pro Gly
        115                 120                 125

Gly Phe Ala Glu Tyr Ile Ile Val Pro His Pro Arg Tyr Leu Val Asp
    130                 135                 140

Ile Ala Gly Leu Asp Leu Ala Glu Ala Ala Pro Leu Ala Cys Ala Gly
145                 150                 155                 160

Val Thr Thr Tyr Ser Ala Leu Lys Lys Phe Gly Asp Leu Ile Gln Ser
                165                 170                 175

Glu Pro Val Ile Ile Gly Ala Gly Gly Leu Gly Leu Met Ala Leu
            180                 185                 190

Glu Leu Leu Lys Ala Met Gln Ala Lys Gly Ala Ile Val Val Asp Ile
        195                 200                 205

Asp Asp Ser Lys Leu Glu Ala Ala Arg Ala Ala Gly Ala Leu Ser Val
    210                 215                 220

Ile Asn Ser Arg Ser Glu Asp Ala Ala Gln Gln Leu Ile Gln Ala Thr
225                 230                 235                 240

Asp Gly Gly Ala Arg Leu Ile Leu Asp Leu Val Gly Ser Asn Pro Thr
```

-continued

```
                245                 250                 255
Leu Ser Leu Ala Leu Ala Ser Ala Ala Arg Gly Gly His Ile Val Ile
            260                 265                 270
Cys Gly Leu Met Gly Gly Glu Ile Lys Leu Ser Ile Pro Val Ile Pro
        275                 280                 285
Met Arg Pro Leu Thr Ile Gln Gly Ser Tyr Val Gly Thr Val Glu Glu
    290                 295                 300
Leu Arg Glu Leu Val Glu Leu Lys Glu Thr His Met Ser Ala Ile
305                 310                 315                 320
Pro Val Lys Lys Leu Pro Ile Ser Gln Ile Asn Ser Ala Phe Gly Asp
                325                 330                 335
Leu Lys Asp Gly Asn Val Ile Gly Arg Ile Val Leu Met His Glu Asn
            340                 345                 350
```

<210> SEQ ID NO 25
<211> LENGTH: 903
<212> TYPE: DNA
<213> ORGANISM: Acinetobacter sp.

<400> SEQUENCE: 25

| | | | | | |
|---|---|---|---|---|---|
| atgaatagca | cacaaagcaa | tactcaattt | cttttcgatt | tatatgcgaa | ctggtcaaga | 60 |
| cggatgcagg | aaaatccgaa | tatgaccatt | gaagactttc | gcagtatgtt | tgatgaatgg | 120 |
| catcaaccta | cattggaacc | ggaagaagtg | tcttataaat | tcgatgttgt | ggcaggtgta | 180 |
| gaaggtcttt | ggatttatcc | gaaagatgct | gacttatcca | agtcatcat | ttatacccat | 240 |
| ggcggtggat | tgcggtcgg | ttcttcggcc | agtcaccgta | agctggtggg | gcatttggcc | 300 |
| aagtatttag | gggtatccgc | atttgtggtt | gattaccgac | gttcaccaga | acatgtcttc | 360 |
| ccggcacaaa | ttcaggacgt | gacagcagta | tataaagaac | tactccagcg | tggctttact | 420 |
| gcaaaaaata | tgctgaccgc | agggattct | gcgggggga | atctggcgat | atcaaccgta | 480 |
| ctcaatctac | gaaatgaagg | gattgagttg | ccaggagcag | tgattgcatt | ctctccttgg | 540 |
| ctggatatgg | agcacaaagg | tgaaaccctg | atcagcaacg | atgccactga | tgccttgatt | 600 |
| acagtggatc | tgcttaaagg | catgtcacaa | atgttcttgg | gtgaacatgg | tgatccggca | 660 |
| aatccattgg | cgaatccgtt | aaaagccaat | tatcaggttt | tcccacgttt | gtatatcaat | 720 |
| gccggatcag | ttgaatcact | tgtagacaat | gcaacacgtc | ttgctgatat | tgcaaaaaaa | 780 |
| gagggtgttg | atgtgacttt | atctgtggtg | gacaacatgc | agcacgtttt | tccttttccta | 840 |
| gctgggcgtg | caagtgaagc | tgatcaagaa | ttagcgaaaa | ttgcgcagtg | gtttaaagca | 900 |
| taa | | | | | | 903 |

<210> SEQ ID NO 26
<211> LENGTH: 300
<212> TYPE: PRT
<213> ORGANISM: Acinetobacter sp.

<400> SEQUENCE: 26

```
Met Asn Ser Thr Gln Ser Asn Thr Gln Phe Leu Phe Asp Leu Tyr Ala
1               5                   10                  15
Asn Trp Ser Arg Arg Met Gln Glu Asn Pro Asn Met Thr Ile Glu Asp
            20                  25                  30
Phe Arg Ser Met Phe Asp Glu Trp His Gln Pro Thr Leu Glu Pro Glu
        35                  40                  45
Glu Val Ser Tyr Lys Phe Asp Val Val Ala Gly Val Glu Gly Leu Trp
    50                  55                  60
```

```
Ile Tyr Pro Lys Asp Ala Asp Leu Ser Lys Val Ile Ile Tyr Thr His
 65                  70                  75                  80

Gly Gly Gly Phe Ala Val Gly Ser Ser Ala Ser His Arg Lys Leu Val
                 85                  90                  95

Gly His Leu Ala Lys Tyr Leu Gly Val Ser Ala Phe Val Val Asp Tyr
            100                 105                 110

Arg Arg Ser Pro Glu His Val Phe Pro Ala Gln Ile Gln Asp Val Thr
        115                 120                 125

Ala Val Tyr Lys Glu Leu Leu Gln Arg Gly Phe Thr Ala Lys Asn Met
    130                 135                 140

Leu Thr Ala Gly Asp Ser Ala Gly Gly Asn Leu Ala Ile Ser Thr Val
145                 150                 155                 160

Leu Asn Leu Arg Asn Glu Gly Ile Glu Leu Pro Gly Ala Val Ile Ala
                165                 170                 175

Phe Ser Pro Trp Leu Asp Met Glu His Lys Gly Glu Thr Leu Ile Ser
            180                 185                 190

Asn Asp Ala Thr Asp Ala Leu Ile Thr Val Asp Leu Leu Lys Gly Met
        195                 200                 205

Ser Gln Met Phe Leu Gly Glu His Gly Asp Pro Ala Asn Pro Leu Ala
    210                 215                 220

Asn Pro Leu Lys Ala Asn Tyr Gln Val Phe Pro Arg Leu Tyr Ile Asn
225                 230                 235                 240

Ala Gly Ser Val Glu Ser Leu Val Asp Asn Ala Thr Arg Leu Ala Asp
                245                 250                 255

Ile Ala Lys Lys Glu Gly Val Asp Val Thr Leu Ser Val Val Asp Asn
            260                 265                 270

Met Gln His Val Phe Pro Phe Leu Ala Gly Arg Ala Ser Glu Ala Asp
        275                 280                 285

Gln Glu Leu Ala Lys Ile Ala Gln Trp Phe Lys Ala
    290                 295                 300
```

<210> SEQ ID NO 27
<211> LENGTH: 17417
<212> TYPE: DNA
<213> ORGANISM: Acinetobacter sp.

<400> SEQUENCE: 27

```
ctagcattta cgcgtgaggt aggtgggtag gtctgtaatg tgaagatcta cgaggaaatc     60
ggcgtcatga cgtgaggtcc agcgaaccgt cttgcgtaat ccgtcattca tggtgagtaa    120
cattgcccgt atttcgcgtt cagtatatag cagaccagca tgattaacga gatcctgggt    180
attttagtcc ggacacccaa agtcccatgc ggtcgccaga tccagtaagt cgactacgac    240
ttgctcatct gtagccaacc ccgcaatcac ttccacaatt tcatcagtg gaaccggatt     300
gaagaaatgg aaacctgcga tacggccctg atgctgacac gcagatgcaa ttgaggtcac    360
agatagtgag gatgtatttg aaaccagaat agtttcttca gccacaatcc tttcaagctg    420
tttaaacaaa gtttgcttga tttccagatt tcaataatt gcttctacga ccagatcaac     480
gccagcaacc tcttcaatgc tttccaagat aatcaatcgg gctaaggtat ccacaagctg    540
ctgttcggtt aactttcctt tagcagctag tttgtgcaag gttactttta attttccaa     600
gccttgctca gcagcgccgg gtttagcatc aaataaacgg acctcaacac cgcctgtgc     660
tgcaatttgc gcaatacccca ttcccattac gcctgtgcca atcaaggcca ttttttgaat   720
cgtcatgact tattttcctt gatattgagg gcttcgcttt tcgaaaaagg cattgacgcc    780
```

-continued

```
ttcttttttga tcttgtgtat caaataaaat ttggaaggct ttacgctcta atgccaaagc      840
accatcgagt ggcatattgg cacctagtgt tgtgacttct ttgatctgtt caacggcaat      900
cggtgagagt tgggcaatct gtgtcgcaat ttcaaccgct ttagcaaggg tttgatcatc      960
ctcaaccact tcggaaacca accccatttt gtcagcttct tctgcagaaa agatctttcc     1020
tgttaacact atttgcatgg ctttaaactt ccctaccgca cgcagtaagc gttgggtacc     1080
accagcacct ggcatcagcc ccaatttgac ttcaggctga ccaaactggg ctgattttcc     1140
ggcaataatg atgtctgcat gcattgcaag ttcacaccca ccacccaatg catatccatt     1200
cacagcagcc acaatcggtt tagggcaatc aataatggcc cgccagtact gttccgtatg     1260
gcgtaaatac atgtctacgg tttttgcagt ggtgaagtcc cggatatccg cacctgctgc     1320
aaatactttt tcaccaccag taatgacaat tgcgcggact gtatcagatg cagcgagctg     1380
ctcaaacatt gctgcgagct gttggcgcag ttccagattc aatgcatttc tagtatctgg     1440
acgatgtagt tcaacaatgg ccacaccatt actttgaata tctaaattca atatttcatt     1500
ttccataaca acctacatgt ttcgcatagc ggtttattta aaccaaatat acctgttttt     1560
ttgcaacaat aaagcccaca ggaacatagt tttaaattaa aaattggcta aaaatatttta    1620 aaaaacacaa ataaaatacc gcacagcggt atttgatatc aatattattg catttatttt     1680
tccattctgt catattattt tcattccaaa gcattagatc accctgcat gaagcagaga      1740 tggctaaatt tacctatcta atacaagggc ttaaaaatga ttcgcgatca agacacatta     1800
aatcagctgg ttgacatgat ccgtcagttt gtcgatggcg ttcttattcc caatgaagaa     1860
attgttgcgg aaaccgatga aattccagct gaaatcgtgc agcaaatgaa agaactgggt     1920 cttttttggtc tcaccattcc tgaggaatat gagggtcttg gcctgaccat ggaggaagag    1980
gtttacattg catttgaact gggacgtacc tctcctgctt tccgttcact gatcggcact     2040
aacaatggga tcggttcatc aggcttaatt attgatggct ccgaagagca gaaacagtat     2100
tttttgccac gtctggcaag tggtgaaatt attggttcat tctgtttaac tgaacctgat     2160
tccggttcag atgctgcctc tttaaaaacc acagcggtga agatggtga tcattacatt      2220 ttaaatggca ctaagcgtta catcaccaat gcaccgcatg cgggtgtctt tactgtcatg     2280
gcacgtacca gtaccgaaat taaaggtaca ggtggaattt cagcctttat cgtggacagt     2340
aaaactcctg gtatttcctt gggtaaacgt gataagaaga tgggccaaaa aggtgcacat     2400
acctgtgatg tgattttga aaactgtcgt attcctgcat ctgcactcat tggtggtgtt      2460
gaaggtgtag gttttaaaac tgcaatgaag gtacttgata aaggccgtat tcatattgct     2520
gcattaagtg taggtgctgc tacgcgtatg ctggaagatt ccctacaata tgccgttgag     2580
cgcaaacagt ttggtcaagc gattgcgaac ttccagttga ttcaaggtat gttagccgat     2640
tctaaagctg aaatttacgc agcaaaatgt atggtattag atgctgcccg acttcgtgat     2700
gctggacaga atgtcagcac ggaagcatct tgtgccaaga tgtttgccac tgaaatgtgt     2760
ggccgtgtcg cagatcgtgg cgtacagatc catggtggtg cgggttatat cagtgaatat     2820
gctattgagc gttttaccg tgatgtacgt ttattccgtt tgtatgaagg tacaacgcaa      2880
atccaacagg tcattattgc ccgcaatatg atccgtgaag cgactcaata attgtataac     2940
aggtattgag tgtatctaaa aggacgggat tagtgattta agctataact tgaatactaa     3000
tcctgacttt ttgatggcaa ggctataaaa cctcctagct cattttatct ctaagctaat     3060
cacagctgaa agatattttc agtcttcatc cttaccagac agttcacaat acaaaattgg    3120
```

-continued

```
attttatgaa tatgcaagaa caagaaatcg aacgcgaatc aatggagttt gacgtcgtga    3180
ttgtcggcgc aggaccggcc ggtctttctg cagcgatcaa gatccgtcaa cttgcaattg    3240
aaaacaacct gaacgatctg tcggtttgtg tggtggaaaa aggctctgaa gtcggtgcgc    3300
acatcttgtc cggtgcggta ctggaaccac gtgccatgaa tgagctgttc ccgaactgga    3360
aggaagaagg tgcaccttta aatgttccag tgaccgaaga caagacctat ttcctgctct    3420
cggatgaaaa atcacaagaa gcgccacact ggatggtgcc taaaaccatg cataacgatg    3480
gcaactatgt tatctcgctc ggcaacgtag tgcgctggtt gggtcaaaaa gcggaagagc    3540
tggaagtatc tattttcccg ggctttgccg ctgctgaaat tctgtaccat gcagatggtt    3600
cggtgaaagg cattcaaacc ggtgacatgg gcattggcaa ggatggcgaa ccgacccata    3660
actttactcc gggctatgaa ctgcatgcca aatacaccct gtttgctgaa ggctgccgtg    3720
gccacctcgg caagcgttta attgccaaat acaacctcga taaagattca gatccacaac    3780
attacggtat cggtatcaaa gagctgtggg aaatcgaccc ggcgaaacac aagccaggtc    3840
tggtgatgca cggtgccggc tggccattgt ctgaaaccgg ttcttcaggc ggctggtggt    3900
tgtatcatgc ggaaaacaat caggtgactt tgggcatgat cgtcgatctg tcttacacca    3960
acccgcatat gtatccgttt atggaaatgc agcgctggaa aacccatccg ctgatcaagc    4020
agtatctgga aggtggcaaa cgtatttctt atggcgcgcg tgcggtaacc aaaggcggct    4080
ttaactcgct accgaaattt accttcccgg gcggatcgct gattggtgac gatgccggct    4140
tcctgaactt tgccaaaatc aagggctcac ataccgcgat gaaatccggc atgctctgcg    4200
gtgaagcagt gtttgaagcc attgctgccg gtgtggaaaa aggtggtgac cttgcggttg    4260
cgcgtgtgac ggaaggcgaa gacttgtttg ccaaaaaact gacttcttac accgacaagt    4320
tcaataatag ctggctgaaa gaagagctgt acaactcgcg taactttggc ccggccatgc    4380
acaagtttgg tcagtggctc ggtggtgcgt ttaactttat cgaccagaac gtgtttaagg    4440
tgccgtttac cctgcatgac ctggtgacgg atttcggtgc gctgaaaacc gtcgatgcgg    4500
tgaacttcaa gccgaattat ccaaaaccgg atggcaaact gaccttgac cgtctgtctt    4560 cggtgtttgt atccaacacg gtgcatgaag aaaaccagcc agcgcattta aaactgactg    4620
acacttcgat tccggtgaat gtcaacctgc caaaatggga tgaaccggcg cagcgctact    4680
gccccgcggg tgtatacgaa atcatggaaa atgatgacgg ttcgaaacgc ttccagatca    4740
atgcagccaa ctgtgtgcac tgcaagacct gtgacatcaa ggatccttca cagaacatca    4800
cctgggtaac accggaaggt ggtggtggtc caaactatcc gaatatgtaa gtctaatcac    4860
ttcaaggaag aggtttccca tttcccttct ttctagcaga tgaagaagct tgcaactaaa    4920
agagattgtt tggatcagtt acccaaaatc gttgaaaaga ttttaactct tcgattttta    4980
ttttttaggt aatcctagcc ctctcggggg ctaggattaa aaattttaag ttattccaac    5040
acgaatgaca aattgttcaa tgcaaaataa aaacatacaa tatataaata tatttttaa    5100 ttaaaacata agattacaat aaaataagaa ttttttattg gagtttgttt tttttctaca    5160
atgatcatta tgtacaattt ttaggttcac cccatccaag ccttgtgatt gcattcctgc    5220
gattctttat tcaatgaata agcaatgcta ttaatcagca atgaataacc agcactgcag    5280
attttgaata aattcacatg tcgtaatgga gattatcatg tcacaaaaaa tggattttga    5340
tgctatcgtg attggtggtg gttttggcgg actttatgca gtcaaaaaat taagagacga    5400
gctcgaactt aaggttcagg cttttgataa agccacggat gtcgcaggta cttggtactg    5460
gaaccgttac ccaggtgcat tgtcggatac agaaacccac ctctactgct attcttggga    5520
```

```
taaagaatta ctacaatcgc tagaaatcaa gaaaaaatat gtgcaaggcc ctgatgtacg    5580
caagtattta cagcaagtgg ctgaaaagca tgatttaaag aagagctatc aattcaatac    5640
cgcggttcaa tcggctcatt acaacgaagc agatgccttg tgggaagtca ccactgaata    5700
tggtgataag tacacggcgc gtttcctcat cactgcttta ggcttattgt ctgcgcctaa    5760
cttgccaaac atcaaaggca ttaatcagtt taaaggtgag ctgcatcata ccagccgctg    5820
gccagatgac gtaagttttg aaggtaaacg tgtcggcgtg attggtacgg gttccaccgg    5880
tgttcaggtt attacggctg tggcacctct ggctaaacac ctcactgtct ccagcgttc    5940
tgcacaatac agcgttccaa ttggcaatga tccactgtct gaagaagatg ttaaaaagat    6000
caaagacaat tatgacaaaa tttgggatgg tgtatggaat tcagcccttg cctttggcct    6060
gaatgaaagc acagtgccag caatgagcgt atcagctgaa gaacgcaagg cagttttga    6120
aaaggcatgg caaacaggtg gcggtttccg tttcatgttt gaaactttcg gtgatattgc    6180
caccaatatg gaagccaata tcgaagcgca aaatttcatt aagggtaaaa ttgctgaaat    6240
cgtcaaagat ccagccattg cacagaagct tatgccacag gatttgtatg caaaacgtcc    6300
gttgtgtgac agtggttact acaacacctt taaccgtgac aatgtccgtt agaagatgt    6360
gaaagccaat ccgattgttg aaattaccga aaacggtgtg aaactcgaaa atggcgattt    6420
cgttgaatta gacatgctga tatgtgccac aggttttgat gccgtcgatg caactatgt    6480
gcgcatggac attcaaggta aaacggctt ggccatgaaa gactactgga agaaggtcc    6540
gtcgagctat atgggtgtca ccgtaaataa ctatccaaac atgttcatgg tgcttggacc    6600
gaatggcccg tttaccaacc tgccgccatc aattgaatca caggtggaat ggatcagtga    6660
taccattcaa tacacggttg aaaacaatgt tgaatccatt gaagcgacaa agaagcgga    6720
agaacaatgg actcaaactt gcgccaatat tgcggaaatg accttattcc ctaaagcgca    6780
atcctggatt tttggtgcga atatcccggg caagaaaaac acgtttact tctatctcgg    6840
tggtttaaaa gaatatcgca gtgcgctagc caactgcaaa aaccatgcct atgaaggttt    6900
tgatattcaa ttacaacgtt cagatatcaa gcaacctgcc aatgcctaaa tatatggggg    6960
gcatccccca tattccattt tgtttaacat cagtcatatg ccagggatgt cttatcatga    7020
actatccaaa tataccttta tatatcaacg gtgagtttct agatcatacc aatagagacg    7080
tcaaagaagt ttttaatcca gtgaaccatg aatgtattgg actcatggcc tgtgcatcac    7140
aagcagacct ggactacgca cttgaaagtt cacaacaggc ttttctaagg tggaaaaaaa    7200
cttctcctat cacccgtagt gaaatcctca gaacctttgc gaaactagcg cgtgaaaaag    7260
cagcagaaat cgggcgcaat attacccttg atcaaggtaa gcccctgaaa gaagccattg    7320
cagaagtcac tgtctgtgca gaacatgcag aatggcatgc agaagaatgc gacgcatttt    7380
atggccgtgt tattccaccg cgtaacccaa atgtacagca actagtagtc agagaaccgc    7440
tgggcgtatg tctggcattt tcaccgtgga atttcccgtt taatcaggca attcgtaaaa    7500
tttctgctgc aattgctgcc ggctgcacca tcattgtgaa aggttctggc gacacaccaa    7560
gcgcggtata tgcgattgcc cagctatttc atgaggcggg tttgccgaat ggtgtgctga    7620
atgtgatttg gggtgactca aacttcattt ctgattacat gatcaaatcg ccgatcatcc    7680
aaaagatttc attcacaggc tcaaccccgg tgggtaaaaa attagcctcg caagcgagtc    7740
tgtatatgaa gccttgcacc atggaattgg gtggtcatgc accggtcatc gtctgtgatg    7800
atgctgatat tgatgccgct gttgaacatc tggtcggtta taaattccgt aatgcaggac    7860
```

-continued

```
aggtctgtgt atcaccaacc cgtttttatg tgcaggaagg tatttataag gaattttctg    7920
agaaagtggt gttaagagcc aaacagatca aagtgggttg tggcttagac gcatcctcag    7980
atatgggacc attggctcaa gctcgccgca tgcatgcaat gcaacaaatt gttgaagatg    8040
cggttcataa aggctcaaaa ttactgcttg gcggaaataa aatttctgac aaaggcaatt    8100
tttttgaacc aacggtactc ggtgacttgt gcaatgacac ccagtttatg aatgacgagc    8160
catttggtcc gatcattggt ttgataccct ttgacacaat agaccatgtc ctggaagaag    8220
caaatcgatt accatttgga ttagcctctt acgcttttac cacatccagc aaaaatgcgc    8280
atcaaatctc atacggactg gaggctggca tggtttcgat taaccacatg ggattggcgc    8340
tcgctgaaac accttttggt ggtattaagg atagcggttt tggtagtgaa gggggtatcg    8400
aaacctttga cggttacctc agaaccaaat ttattacgca actcaattag aaatggatct    8460
tggtgtgcgt aggcacacca attctctttt gactttaagg atgaaagtta aatgagcaca    8520
gacaaagcaa atacgctgat caaacccgaa gatgtcgtgt tatggattcc gggtaatgtc    8580
acaattgaca gcatgaatgc cggttgggaa acattgcaa tcagagggta cgaatatacc    8640
aacctcgatg tgcatattcc tgccatgcgt gactacatga tcgtcaacta taaaaaaagt    8700
gcggcgaaa tgcgtagaaa aggcgatgcc tcttgggata cccaagtggt taagccgggt    8760
tatgtctcct tgttgacctg tggtgaagat tcccgctggg cgtggaatga ccatattgcc    8820
gtcacccatg tctacatttc gcatgactcc atcacctcaa tggcgaataa ggtgtttgat    8880
tatgatatcg cttcgatccg aatcagagac gaagtcggtg tggaagatca tgttttacct    8940
gctctgactt cacttttaga actagaatta agcaaggtg gtttaggtgg aaacctgtat    9000
ttagagagca ttaaaaacca gatcgccctg catttactcc gtcagtatgc caaattagat    9060
tttaaggaag gacagtgccg ttctggtttt actcccctac aacgcagact gttattagaa    9120
tttatcaatg aaaacatgag cattaaaatt accctcgaag atttagcggg attagtcaag    9180
atgagcgtgc ctcatttaat gagaaaattt aaagtcgatt ttggtaattc ccctgctgcc    9240
tacatcatga atctcagggt gcaatttgct aaacgtttgc tcacttcaaa aaagaaattt    9300
ccactgaaag tgattgccag tgaagccggt ttttgcgatc agagccatat gacccgagta    9360
tttcaaaaat tttttgggaa aacacccatc gaaatcagac aggaacacac caatctcgtg    9420
tctgaaaatt cagtctcctc tattgttttt tgagtactaa gagccacgca agaacctgat    9480
tttcaataaa gcatccactg aaaaccagtg tggacttaca tgcattattt atgcaaaata    9540
acaaatgtca tgtgagtatc aagatatact ttctatcgct atcaagaact tgccagtaca    9600
ggcaatatgg atgcactcat caaccagagt cgcagaactc caaatttaaa aaaccgagtg    9660
gatgagcaaa ctgaataagc tgttgttgat tttgcaatcc aatatccagc ttatggtcag    9720
catcggacca gtaatgagct acgtcagatt ggcatcttcg tatctggcag cggtgtgcgc    9780
tctatctggc ttagacacaa tcttgagaat ttcaaaaagc gattaaaggc acttgaaatt    9840
aaagttgctc aagaaggcat tcagttgaat gatcagcaga ttgccgcatt agaacgtaaa    9900
catgaagatg atgttgcttg tggtgaaatt gaaacacatc atccaggtta ccttggagca    9960
caagatactt tttatgtcgg aaatctaaaa ggtgttgggc atatttatca gcaaactttt   10020
attgatactt atagcaaagt ggttcactgc aagctgtaca caaccaagac accaatcaca   10080
gccgcagatt tattgaatga ccgcgtgtta ccattctatg agtcacaagg attgccaatg   10140
cttcgcattt tgaccgacag aggcaccgaa tattgcggta aagttgaaca tcacgattat   10200
gagctttatt tggctctgaa tgatattgat cacactaaaa ctaaagcagc atcaccacaa   10260
```

```
acaaatggga tctgtgagcg cttccataag acgatcttgc aggagtttta tcagattact   10320
tttcgaaaga aactctatag ctcattagaa gagttacagc ttgatctaga cggttggctg   10380
aaattctata atactgaacg aacccatcag ggtaaggtgt gtaatggcag atgagcagca   10440
ttgctgcgca agattgcaac attacttgat ggaaaacgta tttgggctga aaagaattta   10500
gttcaaattt aacctgacag tcttaagcaa atatcggtaa ctatcagatc aggtttgaga   10560
taccgtctga aacgtcaagt aaatgattga gaattcatgc tcaataatct gcttgataag   10620
gctgttggtg tttgagcaca ccataacaaa gatgaatcaa cttcctcatc gcggctccaa   10680
tcgctatcat cttggtttta ccattcgcca ataaacgttc attcattgcc ctgatgtgag   10740
ggttatgccg agttgcgaca atggctgcca tatataaacc agcacgtatt ttggaagagc   10800
ccgcttggga taaacggctt ctgccatgaa tggaactacc cgattgcttt tgaatgggga   10860
ccaaaccgac aaaggcagcc gcttgactag cccttcaaa agtatggctg cgcaagaaac   10920
tgagcattaa taaactggtt cgatctgcaa tggctggaat actgctgagc agttctttat   10980 catttttaa atcaggattc tgattaatgt gatcatcaat ttgctggtcg ataccctgaa   11040
tgtgtttgtt taactgttca atactcttgt ggatagactg aagtacaggt tccatcgtga   11100
aggtcgactc tgcttttcc aaacgattct tttcacgttg taaatcttca caagaatag   11160 ctcttctatc cagcaaagca ttcagcaatt gaatatgttt aggtaaaggt tgccaaaaat   11220
gtagatcggc agtcatcgca aatcgagcta ggacctcact atccaccttg tctgttttat   11280
tcagcttaga catactctga gcaaaatatc gagctctggc aggattggtt acacagactt   11340
gatagcccgc atcaaataaa tatttaacca agagttcatg ataaatagat gttgcttcca   11400
ttaaaataat ggtctgcgta aagttgcag catgctgctt tagccaggtt tgaagttgct   11460
caaacccttt tggtgtattt gaaaagttt tggttttctt tttatttgca gaattttcta   11520
aaattaaaca gcaatcaatt ttagctttag caacatcaat accaagataa acataatct   11580 ttacctgctt tatttatcca attattgttt tagcataacc accgtcttt cttgtgaatg   11640 cagcatcaaa gtgcttgtta ccgtccagag ttgtgcaagt ggttagggca aattacaggt   11700
tttatctcaa actctaactt tatgttttgc tagtacacga aactctgcaa tttgcaatat   11760
agtgatagct aatcactatg aatggtaaga tacaagctag tacacataag aagatattac   11820
ttcttctcag gcagattcgc agcaaagaaa aattttccct tacaacaata gataaaagaa   11880
aagagggtat cacccctctt tcctctttat atgggggtat cttctactca tttttttattt   11940 cgaggtatat gcaccatcga ccacatactg actaccggtc acaaatgaag catcatcaga   12000
aagtaggaag gcaacaacct gagcaacttc ttccggctgt cccaaacgac caatcggatg   12060
tagttttacc atttctgctt cttcaaattc tgcaatcaaa ggcgttttga tatagccagg   12120
atgtactgaa ttaatgcgaa tccctttatc tgcatattcc aatgccgccg ctttcgttag   12180
acccgttacg ccatgttttg cagcgacata gcctgaaata ttttgaatcc cgatcaagcc   12240
tgcaatagaa gcggtattga caatcgctcc gcccctgcg gccaagattg caggaacttc   12300
ataatgcatg ctgtagaaaa ccgcattcaa gttcacatca atcacacgac gccatccttc   12360
aatgctcaat tcttcggtgg agttaacttc acccagaatt cccgcattat tgaaggccaa   12420
atgcagtgca ccaaaagtgc tgaccgcaaa ctcgactgca gctttcatgt cttcaggctc   12480
agcagtattg gccttattcg cagccgcttt cccgcctaaa gcgacaattt cgtccacaac   12540
tttctgtgct gcttccaggt taatatctga aaccactaca cttacaccct gttgagccaa   12600
```

```
aagcagtgcg gtgcttttac caatacctga accagcgcca gtaattaaag cgactttatt    12660
gttgaattta tttgacataa ttttttccat ttcaaatttt aagcatcaaa gcttgtttca    12720
tattttaaga ttcaagaaac cagatccggt agatgactcg tctgccaagc gacaacccgt    12780
ctgatatcag gcttgcgatt caccctgtag acggttttca ttcctaaatt ctgtatttcc    12840
aagttatata aacaaaagtg ctaatctatg gggaattccc aggatccaaa caaatagaat    12900
gccatgaaag catcttttgc caagcgctgt gctgtatgtt tcctagacaa accaccaacg    12960
ataactgcaa cttttttgaac tccttacaat ttccttatttt tctttcccct tcatcgcata   13020
aaaatagttt ttgcattcac aacaaaatca gcatgaatag ttttttaaact cactgtacat    13080 attttctata ttgatgacca agctggatat tgaattgcaa aattctatac agcctgttca    13140
acatgatcga tttagaaggc atacagtaaa cgtgactgaa gtccagaaat ttccaagcca    13200
ttttcaacat tcacatcttg tcgccattgt aataatagct gcagattcgg cttgatattg    13260
gtagaagcag aaacgacaaa ggtatctttt ctatcactgc cacgttcagt gacaccattc    13320
accttttctt taccgccatc ggtatgtctc caggtgacag ccaaattgga tttatcggtc    13380
actttataga gtgcggagaa atctgtctgg aaaaaaacct ctttctcaat gttggtatat    13440
ttttgctcgc tataaagttc aaactgcccc acccccctcaa gcgcaaattt atcagttaaa   13500
gcatggtaat aaccggcctg aacattatat tgatagcgat cattactgat ggcaaaaccc    13560
ttcgtttcat tactgccggt aggtacggtc aaaaaaccac cgaaaccaaa atagcgccct    13620
ttttcagcat catgcaatgg ccaggcgata ccacccacaa ttaaatcacc gacacccgag    13680
atatcatcag cgccattcat ctttttgcttg gcaaaaggca agaggaattg aggatctaca    13740
atccaatccc ctacttcaat aaaacgaacg taacgcaata ttcccaaatc aatgcttaaa    13800
tcgagatcat cagcgacttt atcaccattt gcatacgcct tatccgcttc cgtatgctgg    13860
taataggcaa ccgctaagtt ggttccccct ggaagtgctt gataatcccc ggcatcagaa    13920
ctcacccctg cggcttgcag gtccaaagcg gcagttaaag caaagaccaa agcagctatt    13980
ttttgatttg aacgatgata gaaatagttt ttcatttgtt tcattttttaa ctctccgttg    14040 ttttgactca ttttttttaaa atgagtcttc ctagcacaaa gaccactcag gtctttgcgc    14100
aatttcttga ttttgatttg ggtattaaat atggaaaaac gttgggtgat cagttttcgt    14160
gcataagcac aatacgcccg atgacgttgc catctttcaa gtctccaaat gcggaattga    14220
tctgcgaaat tggcagtttt ttcacgggaa tggctgacat gtgggtttct ttcaccagct    14280
ccaccagctc tcttaattcc tctaccgtcc ctacataact gccctggatt gtgagtggtc    14340
tcattggaat caccggaatg gaaagcttaa tttctccccc catcaatccg cagatcacaa    14400
tatgcccacc acgtgcagca ctcgccaagg caaggctcaa tgttggatta ctgccaacca    14460
gatcaaggat cagacgtgca ccaccgtcag ttgcctgaat cagctgttga gcagcatcct    14520
cacttcggct attgatgacc gataatgcac cggcagcacg tgctgcttcc agtttgctgt    14580
catcaatatc aactacgatt gcgcctttgg cttgcatagc tttgagcaac tcgagtgcca    14640
tcagccctaa accaccggca ccaatgatca ccaccggctc gctttgaatc aaatcaccga    14700
attttttcag tgcactgtat gttgtcacgc ctgcacatgc caaggtgca gcttcagcca    14760 gatccagacc tgcaatatcc accagatatc gtggatgcgg cacgatgata tattcggcaa    14820
aaccacccgg cttggcgatg cctaactgtt gcggtttggc acacaggttt tcttcgccac    14880
gtttacagta gttgcattca ccgcaaccaa tccatggatg aaccaagctg accatgccga    14940
ccttgactga ttccgcatct ggaccgacag caaccacctg acctgtaatt tcatgactta    15000
```

```
aggttaaggg tggcttcagc ccacgatctg caagggataa acgcttgccc ccacctagat    15060
cataataacc ttcccataag tgtaaatccg tatggcatag acctgcggct tttacatgga    15120
gtaaaacttc agtacctttc ggttgcggaa tttctttctc aacgtcttcg agtggttgtc    15180
catgatgcgt cacgcagtaa cagtgcatga atctctcctt tgaaacaata aaatagacgg    15240
ccttgtagtg aacaaagtct tttattcact agttttata cgccgtgtgg gcactgattt    15300
atgctttaaa ccactgcgca attttcgcta attcttgatc agcttcactt gcacgcccag    15360
ctaggaaagg aaaaacgtgc tgcatgttgt ccaccacaga taaagtcaca tcaacaccct    15420 cttttttgc aatatcagca agacgtgttg cattgtctac aagtgattca actgatccgg    15480
cattgatata caaacgtggg aaaacctgat aattggcttt taacgattc gccaatggat    15540 ttgccggatc accatgttca cccaagaaca tttgtgacat gcctttaagc agatccactg    15600
taatcaaggc atcagtggca tcgttgctga tcagggtttc acctttgtgc tccatatcca    15660
gccaaggaga gaatgcaatc actgctcctg gcaactcaat cccttcatt cgtagattga    15720 gtacggttga tatcgccaga ttccccccccg cagaatcccc tgcggtcagc atattttttg    15780
cagtaaagcc acgctggagt agttctttat atactgctgt cacgtcctga atttgtgccg    15840
ggaagacatg ttctggtgaa cgtcggtaat caaccacaaa tgcggatacc cctaaatact    15900
tggccaaatg ccccaccagc ttacggtgac tggccgaaga accgaccgca aatccaccgc    15960
catgggtata aatgatgact ttggataagt cagcatcttt cggataaatc caaagacctt    16020
ctacacctgc cacaacatcg aatttataag acacttcttc cggttccaat gtaggttgat    16080
gccattcatc aaacatactg cgaaagtctt caatggtcat attcggatt tcctgcatcc    16140 gtcttgacca gttcgcatat aaatcgaaaa gaaattgagt attgctttgt gtgctattca    16200
ttttaaaatc cttgatttga tatttaagga ataaatccta gttttattcc atgaagatat    16260
aaaaacttga gtgccatcac tcatggctag acactcagaa gatccaaatc taaagagtgg    16320
ctttgcatca ctggtttgat acaattttt gcatgactaa gtaatctacg gataatctaa    16380
ccgtttcaaa ttagtatttt aaaatgtaaa aatacacatc cagcgaatgt tttctgcaaa    16440
atcgcatcct gttcaatata gcttttgatc ctacttattc tcttttctat tccagtccgt    16500
tataaaaaag ctttcattca ttttcatgca atcatgagct atgaatgttc ttaaacatta    16560
aacgattgtg tgtatggctg acttgtacat tcttgtactt atttttgtat aaaatgatca    16620
ggctcatcaa tttatgggaa aaattacaat tcgggtacaa tatctttcct gtttcatgaa    16680
tctattcaac tcattaaact tacgaccctc aactgcccaa aatcatagga tctgccgatc    16740
cacttgcaga attagcaatg ctaaaacatg aactccaaag agttactaaa aaagagcat    16800 attaaaaaaa agccgtggca tatttcgcaa gccagttcaa gtcaggtatg tctttattca    16860
gtacctcagt taaactttag attttcataa cgatggttat tctgcatggc taaatacgct    16920
aatcagcaaa aaactctcca aaagataggc acagaaacac atatcaacca taaaaaccat    16980
ctcagacagt atatttacaa gcctctaatt caccgcactc acacttctct gcaagccttt    17040
ttaaataccc tgtacaaagt tctcagcctg atgaagcttc accttggact tagctttcag    17100
ttcagcctgt acttggtcag tttctgaatt ttcatttgca taaaactcct ccaccacatc    17160
```

-continued

```
catacccctcc tcaatgtcag tttcaaaatg tgcattgtca tagccttgcc gtgccatttg      17220
aatggcttat tgaagattaa tggcatcacg taaagttaaa tccacgtaat acacaggtgt      17280
tcgatagctt tgcgtcgtag actttctcga agagtcaatt gcagcggtag gcatgacagc      17340
aagccattca atgccgcatg gtaataactc agccgtgcgg ccaacgttcg tatgctgtta      17400
aaacccggtt attctaa                                                    17417
```

```
<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:PRIMER

<400> SEQUENCE: 28
gagtttgatc ctggctcag                                                  19
```

```
<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence:PRIMER

<400> SEQUENCE: 29
taccttgtta cgactt                                                     16
```

```
<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence:PRIMER
<221> NAME/KEY: unsure
<222> LOCATION: (11)
<223> OTHER INFORMATION: Y=C OR T
<221> NAME/KEY: unsure
<222> LOCATION: (12)
<223> OTHER INFORMATION: M= A OR C

<400> SEQUENCE: 30
gtgccagcag ymgcggt                                                    17
```

```
<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence:PRIMER

<400> SEQUENCE: 31
gagtctgagc atatgtcaca aaaaatggat tttg                                 34
```

```
<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence:PRIMER

<400> SEQUENCE: 32
gagtctgagg gatccttagg cattggcagg ttgcttgat                            39
```

BIOLOGICAL METHOD FOR THE PRODUCTION OF ADIPIC ACID AND INTERMEDIATES

This is a Continuation-in-Part application, filed under 37 C.F.R. 1.153 (b) and claiming priority to U.S. Ser. No. 09/252,553, filed Feb. 19, 1999 now abandoned.

FIELD OF THE INVENTION

The invention relates to the field of molecular biology and microbiology. More specifically adipic acid has been produced from cyclohexanol by micro-biological means. The reaction is mediated by a set of enzymes resident on a 17 kb gene cluster, isolated from Acinetobacter sp.

BACKGROUND OF THE INVENTION

Production of adipic acid in the U.S. was 1.96 billion pounds in 1997 with an estimated 2.0 billion pounds in 1998. Historically the demand for adipic acid has grown 2% per year and 1.5–2% is expected through the year 2002. Adipic acid consistently ranks as one of the top fifty chemicals produced domestically. Nearly 90% of domestic adipic acid is used to produce nylon-6,6. Other uses of adipic acid include production of lubricants and plasticizers, and as a food acidulant.

The dominant industrial process for synthesizing adipic acid employs initial air oxidation of cyclohexane to yield a mixture of cyclohexanone (ketone) and cyclohexanol (alcohol), which is designated KA (see for example U.S. Pat. No. 5,221,800). Hydrogenation of phenol to yield KA is also used commercially, although this process accounts for just 2% of all adipic acid production. KA produced via both methods is oxidized with nitric acid to produce adipic acid. Reduced nitrogen oxides including $NO_2$, NO, and $N_2O$ are produced as by-products and are recycled back to nitric acid at varying levels.

Research has also focused on synthesis of adipic acid from alternative feedstocks. Significant attention has been directed at carbonylation of butadiene (U.S. Pat. No. 5,166,421). More recently, a method of dimerizing methyl acrylates was reported, opening up the possibility of adipic acid synthesis from C-3 feedstocks.

These processes are not entirely desirable due to their heavy reliance upon environmentally sensitive feedstocks, and their propensity to yield undesirable by-products. Non-synthetic, biological routes to adipic acid would be more advantageous to industry and beneficial to the environment.

A number of microbiological routes are known. Wildtype and mutant organisms have been shown to convert renewable feedstocks such as glucose and other hydrocarbons to adipic acid [Frost, John, Chem. Eng. (Rugby, Engl.) (1996), 611, 32–35; WO 9507996; Steinbuechel, AlexanderCLB Chem. Labor Biotech. (1995), 46(6), 277–8; Draths et al., ACS Symp. Ser. (1994), 577(Benign by Design), 32–45, U.S. Pat. No. 4,400,468; JP 49043156 B4; and DE 2140133]. Similarly, organisms possessing nitrilase activity have been shown to convert nitriles to carboxylic acids including adipic acid [Petre et al., AU 669951; CA 2103616].

Additionally, wildtype organisms have been used to convert cyclohexane and cyclohexanol and other alcohols to adipic acid [JP 01023894 A2; Cho; Takeshi et al., Bio Ind, (1991), 8(10), 671–8; Horiguchi et al., JP 01023895 A2; JP 01023894 A2; JP 61128890 A; Hasegawa et al., Biosci., Biotechnol., Biochem. (1992), 56(8), 1319–20; Yoshizako et al., J. Ferment. Bioeng. (1989), 67(5), 335–8; Kim et al., Sanop Misaengmul Hakhoechi (1985), 13(1). 71–7; Donoghue et al., Eur. J. Biochem. (1975), 60(1), 1–7].

One enzymatic pathway for the conversion of cyclohexanol to adipic acid has been suggested as including the intermediates cyclohexanol, cyclohexanone, 2-hydroxycyclohexanone, ε-caprolactone, 6-hydroxycaproic acid, and adipic acid. Some specific enzyme activities in this pathway have been demonstrated, including cyclohexanol dehydrogenase, NADPH-linked cyclohexanone oxygenase, ε-caprolactone hydrolase, and NAD (NADP)-linked 6-hydroxycaproic acid dehydrogenase (Tanaka et al., Hakko Kogaku Kaishi (1977), 55(2), 62–7). An alternate enzymatic pathway has been postulated to comprise cyclohexanol→cyclohexanone→1-oxa-2-oxocycloheptane→6-hydroxyhexanoate→6-oxohexanoate→adipate [Donoghue et al., Eur. J. Biochem. (1975), 60(1), 1–7]. The literature is silent on the specific gene sequences encoding the cyclohexanol to adipic acid pathway, with the exception of the monoxygenase, responsible for the conversion of cyclohexanone to caprolactone, [Chen,et al., J. Bacteriol., 170, 781–789 (1988)].

The problem to be solved, therefore is to provide a synthesis route for adipic acid which not only avoids reliance on environmentally sensitive starting materials but also makes efficient use of inexpensive, renewable resources. It would further be desirable to provide a synthesis route for adipic acid which avoids the need for significant energy inputs and which minimizes the formation of toxic by-products.

Applicants have solved the stated problem by identifying, isolating and cloning a 17 kb nucleic acid fragment from Acinetobacter sp. that is responsible for mediating the conversion of cyclohexanol to adipic acid. Recombinant E. coli hosts with the DNA containing the 17 kb gene cluster conveys on the host the ability to convert cyclohexanol to adipic acid.

SUMMARY OF THE INVENTION

The invention provides-an isolated nucleic acid fragment encoding an adipic acid synthesizing enzyme selected from the group consisting of: an isolated nucleic acid fragment encoding an adipic acid synthesizing enzyme selected from the group consisting of: (a) an isolated nucleic acid molecule encoding the amino acid sequence set forth in SEQ ID NO:12, SEQ ID NO:20, SEQ ID NO:24, and SEQ ID NO:26, or an enzymatically active fragment thereof; (b) an isolated nucleic acid molecule that hybridizes with (a) under the following hybridization conditions: 0.1×SSC, 0.1% SDS at 65° C.; and washed with 2×SSC, 0.1% SDS followed by 0.1×SSC. 0.1% SDS; (c) an isolated nucleic acid molecule that is completely complementary to (a) or (b).

In another embodiment the invention provides methods for the isolation of nucleic acid fragments substantially similar to those encoding the polypeptides as set forth in SEQ ID NO:12, SEQ ID NO:20, SEQ ID NO:24, and SEQ ID NO:26, based on the partial sequence of said nucleic acid fragments.

The invention further provides a method for the production of adipic acid comprising: contacting a transformed host cell under suitable growth conditions with an effective amount of cyclohexanol whereby adipic acid is produced, said transformed host cell comprising a nucleic acid fragment encoding SEQ ID NO:10, SEQ ID NO:12, SEQ ID NO:20, SEQ ID NO:24, and SEQ ID NO:26 under the control of suitable regulatory sequences.

The invention additionally provides methods for the production of intermediates in the pathway for the synthesis of adipic acid from cyclohexanol comprising transformed organisms transformed with any one of the open reading frames encoding SEQ ID NO:12, SEQ ID NO:20, SEQ ID NO:24, and SEQ ID NO:26.

Additionally, the invention provides host cells transformed with all or a substantial portion of the 17 kb gene cluster.

BRIEF DESCRIPTION OF THE DRAWINGS, SEQUENCE DESCRIPTIONS AND BIOLOGICAL DEPOSITS

Figure 1:
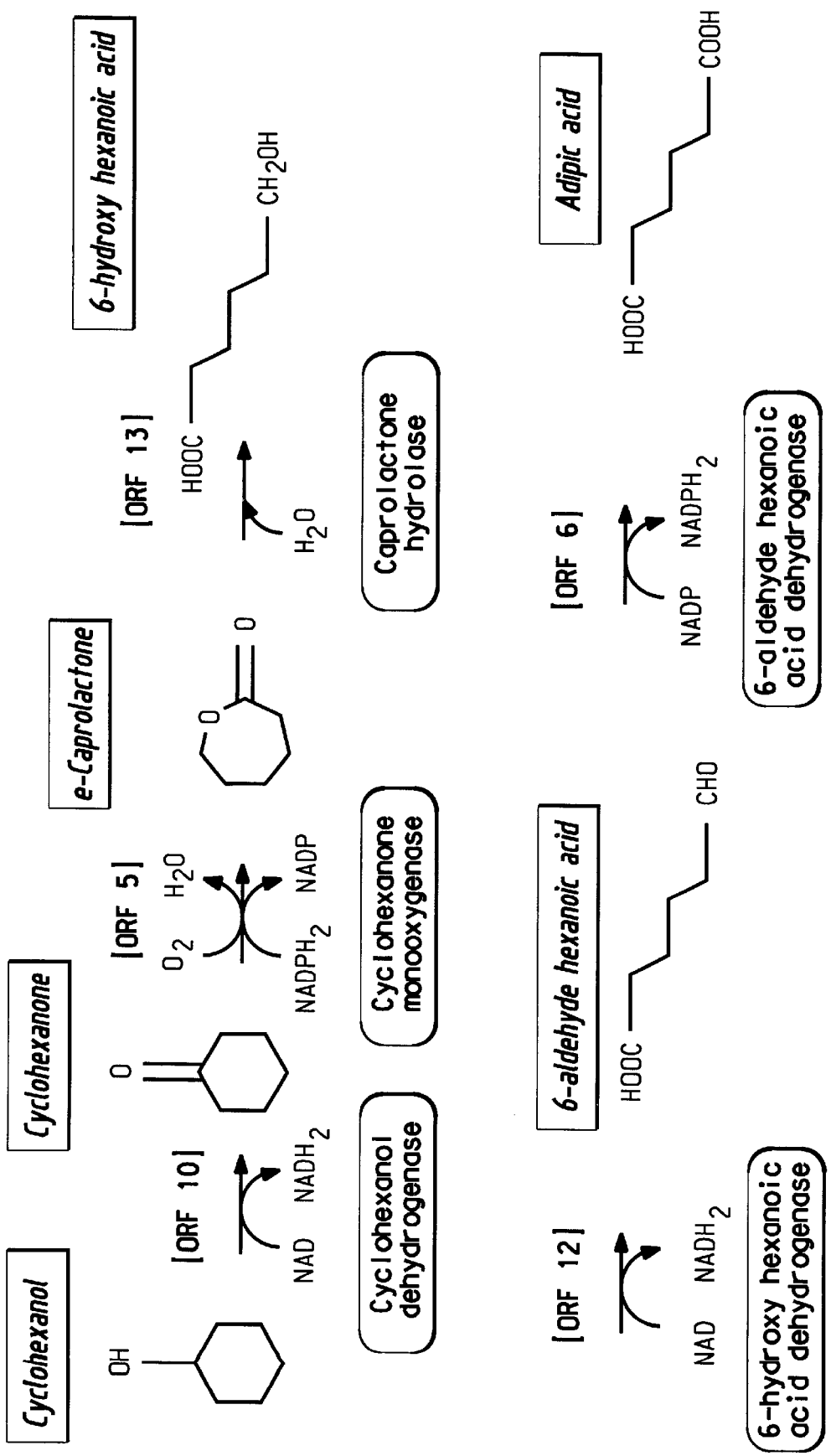
FIG. 1 is a diagram showing the pathway for the conversion of cyclohexanol to adipic acid.
Figure 2:
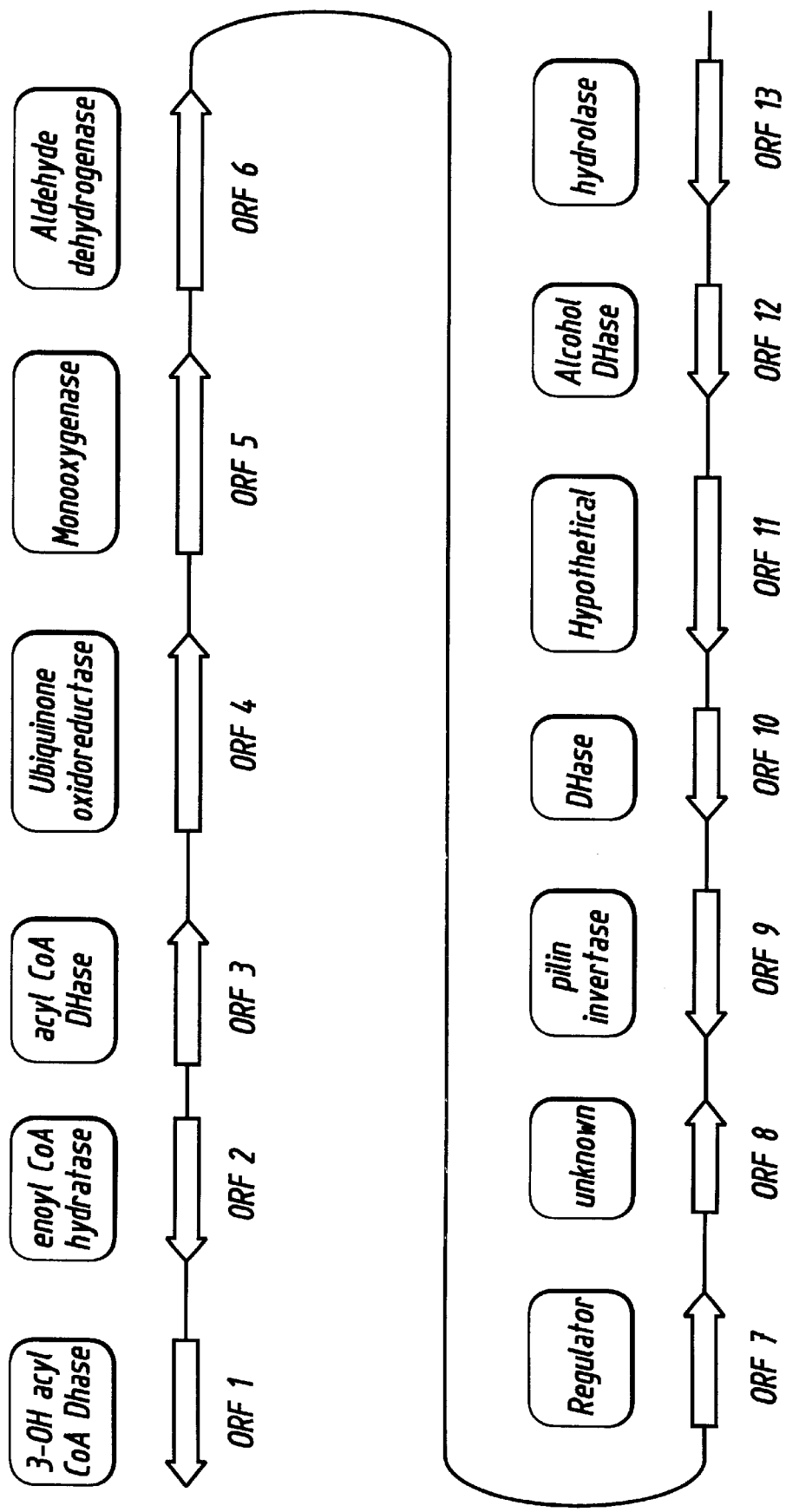
FIG. 2 is a diagram showing the organization of ORF's 1–13 on the 17 kb gene cluster.

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. § 1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. § 1.822.

SEQ ID NO:1 is the nucleotide sequence of ORF 1 encoding a hydroxyacyl CoA dehydrogenase enzyme isolated from a 17 kb nucleic acid fragment from Acinetobacter sp.

SEQ ID NO:2 is the deduced amino acid sequence of ORF 1 encoding a hydroxyacyl CoA dehydrogenase enzyme isolated from a 17 kb nucleic acid fragment from Acinetobacter sp.

SEQ ID NO:3 is the nucleotide sequence of ORF 2 encoding an enoyl CoA hydratase enzyme isolated from a 17 kb nucleic acid fragment from Acinetobacter sp.

SEQ ID NO:4 is the deduced amino acid sequence of ORF 2 encoding an enoyl CoA hydratase enzyme isolated from a 17 kb nucleic acid fragment from Acinetobacter sp.

SEQ ID NO:5 is the nucleotide sequence of ORF 3 encoding a short chain acyl-CoA dehydrogenase enzyme isolated from a 17 kb nucleic acid fragment from Acinetobacter sp.

SEQ ID NO:6 is the deduced amino acid sequence of ORF 3 encoding a short chain acyl-CoA dehydrogenase enzyme isolated from a 17 kb nucleic acid fragment from Acinetobacter sp.

SEQ ID NO:7 is the nucleotide sequence of ORF 4 encoding a ubiquinone oxidoreductase enzyme isolated from a 17 kb nucleic acid fragment from Acinetobacter sp.

SEQ ID NO:8 is the deduced amino acid sequence of ORF 4 encoding a ubiquinone oxidoreductase enzyme isolated from a 17 kb nucleic acid fragment from Acinetobacter sp.

SEQ ID NO:9 is the nucleotide sequence of ORF 5 encoding a monooxygenase enzyme isolated from a 17 kb nucleic acid fragment from Acinetobacter sp.

SEQ ID NO:10 is the deduced amino acid sequence of ORF 5 encoding a monooxygenase enzyme isolated from a 17 kb nucleic acid fragment from Acinetobacter sp.

SEQ ID NO:11 is the nucleotide sequence of ORF 6 encoding an aldehyde dehydrogenase enzyme isolated from a 17 kb nucleic acid fragment from Acinetobacter sp.

SEQ ID NO:12 is the deduced amino acid sequence of ORF 6 encoding an aldehyde dehydrogenase enzyme isolated from a 17 kb nucleic acid fragment from Acinetobacter sp.

SEQ ID NO:13 is the nucleotide sequence of ORF 7 encoding a AraC-like transcriptional regulator protein isolated from a 17 kb nucleic acid fragment from Acinetobacter sp.

SEQ ID NO:14 is the deduced amino acid sequence of ORF 7 encoding a AraC-like transcriptional regulator protein isolated from a 17 kb nucleic acid fragment from Acinetobacter sp.

SEQ ID NO:15 is the nucleotide sequence of ORF 8 having an unknown function isolated from a 17 kb nucleic acid fragment from Acinetobacter sp.

SEQ ID NO:16 is the deduced amino acid sequence of ORF 8 having an unknown function isolated from a 17 kb nucleic acid fragment from Acinetobacter sp.

SEQ ID NO:17 is the nucleotide sequence of ORF 9 encoding a recombinase enzyme isolated from a 17 kb nucleic acid fragment from Acinetobacter sp.

SEQ ID NO:18 is the deduced amino acid sequence of ORF 9 encoding a recombinase enzyme isolated from a 17 kb nucleic acid fragment from Acinetobacter sp.

SEQ ID NO:19 is the nucleotide sequence of ORF 10 encoding a dehydrogenase enzyme isolated from a 17 kb nucleic acid fragment from Acinetobacter sp.

SEQ ID NO:20 is the deduced amino acid sequence of ORF 10 encoding a dehydrogenase enzyme isolated from a 17 kb nucleic acid fragment from Acinetobacter sp.

SEQ ID NO:21 is the nucleotide sequence of ORF 11 encoding a protein of unknown finction isolated from a 17 kb nucleic acid fragment from Acinetobacter sp.

SEQ ID NO:22 is the deduced amino acid sequence of ORF 11 encoding a protein of unknown function isolated from a 17 kb nucleic acid fragment from Acinetobacter sp.

SEQ ID NO:23 is the nucleotide sequence of ORF 12 encoding a NAD-dependent alcohol dehydrogenase enzyme isolated from a 17 kb nucleic acid fragment from Acinetobacter sp.

SEQ ID NO:24 is the deduced amino acid sequence of ORF 12 encoding a NAD-dependent alcohol dehydrogenase enzyme isolated from a 17 kb nucleic acid fragment from Acinetobacter sp.

SEQ ID NO:25 is the nucleotide sequence of ORF 13 encoding a hydolase enzyme isolated from a 17 kb nucleic acid fragment from Acinetobacter sp.

SEQ ID NO:26 is the deduced amino acid sequence of ORF 13 encoding a hydolase enzyme isolated from a 17 kb nucleic acid fragment from Acinetobacter sp.

SEQ ID NO:27 is the nucleotide sequence of the 17 kb gene cluster isolated from a Acinetobacter sp., encoding all the enzymes relevant to the biocoversion of cyclohexanol to adipic acid.

SEQ ID NO:28–31 are primers used for the 16s rRNA identification of the source of the 17 kb gene cluster as an Acinetobacter sp.

SEQ ID NO:31 is the sequence of a primer used for screening the cosmid library of our isolated Acinetobcter sp.

based on homology to the published sequence from Acinet-bbcter NCIB 9871.

SEQID NO:32 is the sequence of a primer used to sequence 16s rDNA for typing the isolated bacterium.

DETAILED DESCRIPTION OF THE INVENTION

The present invention provides new sequences encoding key enzymes in the synthesis of adipic acid from cyclohexanol. The genes and their expression products are useful for the creation of recombinant organisms that have the ability to produce adipic acid while growing on cyclohexanol, and for the identification of new species of bacteria having the ability to produce adipic acid. Full length sequence for 13 ORF's have been obtained and identified by comparison to public databases containing nucleotide and protein sequences using the BLAST algorithms well known to those skilled in the art. The relevant ORF's all reside on a 17 kb nucleic acid fragment and together represent a gene cluster that encodes proteins that are sufficient to mediate the transformation of cyclohexanol to adipic acid. Conversion of cyclohexanol to adipic acid has been observed with recombinant host cells containing the 17 kb nucleic acid fragment.

In this disclosure, a number of terms and abbreviations are used. The following definitions are provided.

"Open reading frame" is abbreviated ORF.

"Polymerase chain reaction" is abbreviated PCR.

"High performance liquid chromatography" is abbreviated HPLC.

"Mass spectrometry" is abbreviated MS.

"High performance liquid chromatography coupled with mass spectrometry" is abbreviated LC/MS.

"3-hydroxybutyryl CoA dehydrogenase" refers to an enzyme that directs the bacterial metabolic intermediate acetoacetyl-CoA toward butyrate or butanol. Within the context of the present invention this enzyme is encoded by ORF1 (designated as fadC) and is resident on the 17 kb Acinetobacter gene cluster, necessary for the conversion of cyclohexanol to adipic acid.

"Enoyl-CoA hydratase" refers to an enzyme that is involved in the degradation of straight-chain fatty acids. Within the context of the present invention this enzyme is encoded by ORF2 (designated asfadB) and is resident on the 17 kb Acinetobacter gene cluster, necessary for the conversion of cyclohexanol to adipic acid.

"Acyl-CoA dehydrogenase" refers to an enzyme that catalyzes the oxidation of straight-chain fatty acids. Within the context of the present invention this enzyme is encoded by ORF3 (designated asfade) and is resident on the 17 kb Acinetobacter gene cluster, necessary for the conversion of cyclohexanol to adipic acid.

"Ubiquinone oxidoreductase" refers to a redox enzyme that functions in proton-translocation of lipid bilayer membranes in prokaryotic and eukaryotic species. Within the context of the present invention this enzyme is encoded by ORF4 (designated as etfD) and is resident on the 17 kb Acinetobacter gene cluster, necessary for the conversion of cyclohexanol to adipic acid.

"Cyclohexanone monooxygenase" refers to an enzyme that catalyzes the conversion of cyclohexanone to $\epsilon$-caprolactone. Within the context of the present invention this enzyme is encoded by ORF5 (designated as chdA) and is resident on the 17 kb Acinetobacter gene cluster, necessary for the conversion of cyclohexanol to adipic acid.

"6-aldehyde hexanoic acid dehydrogenase" refers to an enzyme that catalyzes the conversion of 6-aldehyde hexanoic acid to adipic acid. Within the context of the present invention this enzyme is encoded by ORF6 (designated as chdB) and is resident on the 17 kb Acinetobacter gene cluster, necessary for the conversion of cyclohexanol to adipic acid.

"Recombinase" will mean a protein that mediates site specific recombination of nucleic acid fragments. Within the context of the present invention this enzyme is encoded by ORF9 (designated as chdY, most closely related to pilin gene inverting protein) and is resident on the 17 kb Acinetobacter gene cluster, necessary for the conversion of cyclohexanol to adipic acid.

"Cyclohexanol dehydrogenase" refers to an enzyme that catalyzes the conversion of cyclohexanol to cyclohexanone. Within the context of the present invention this enzyme is encoded by ORF10 (designated as chdC) and is resident on the 17 kb Acinetobacter gene cluster, necessary for the conversion of cyclohexanol to adipic acid.

"6-hydroxy hexanoic acid dehydrogenase" refers to an enzyme that atalyzes the conversion of 6-hydroxy hexanoic acid to 6-aldehyde hexanoic acid. Within the context of the present invention this enzyme is encoded by ORF12 (designated as chdD) and is resident on the 17 kb Acinetobacter gene cluster, necessary for the conversion of cyclohexanol to adipic acid.

"Caprolactone hydolase" refers to an enzyme that catalyzes the conversion of caprolactone to 6-alcohol hexanoic acid. Within the context of the present invention this enzyme is encoded by ORF 13 (designated as chdE) and is resident on the 17 kb Acinetobacter gene cluster, necessary for the conversion of cyclohexanol to adipic acid.

The term "gene cluster" will mean genes organized in a single expression unit or physically associated with each other.

The term "17 kb nucleic acid fragment" refers to the 17 kb gene cluster comprising ORF's 1–13 necessary for the conversion of cyclohexanol to adipic acid.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "adipic acid synthesizing enzyme" means the gene product of any of ORF 5, ORF 6, ORF 10, ORF 12 and ORF 13 SEQ ID NO:9, SEQ ID NO:11, SEQ ID NO:19, SEQ ID NO:23 and SEQ ID NO:25 respectively.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no forrnarnide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those killed in this art. Accordingly, the instant invention comprises the complete equences as reported in the accompanying Sequence Listing, as well as ubstantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular*

*Biology* (von Heinje, G., ed.) Academic Press (1987); and *Seguence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, as used in the instant invention, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad Sci. U.S.A.* 85:2444–2448 (1988). The BLAST X program is publicly available from NCBI and other sources (*BLAST Manual*, Altschul et al., Natl. Cent. Biotechnol. Inf, Natl. Library Med. (NCBI NLM) NIH, Bethesda, Md. 20894; Altschul et al., *J. Mol. Biol.* 215:403–410 (1990)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the bacterial adipic acid synthesizing enzymes as set forth in SEQ ID NOS: SEQ ID NO:10, SEQ ID NO:12, SEQ ID NO:20. SEQ ID NO:24, and SEQ ID NO:26. The skilled artisan is well aware of the "codon-bias" exhibited by a specific host cell in usage of nucleotide codons to specifv a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The nucleic acid fragments of the instant invention may be used to isolate cDNAs and genes encoding homologous enzymes from the same or other bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding similar enzymes to those of the instant adipic acid pathway, either as cDNAs or genomic DNAs, could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant ORF's 1–13 may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding bacterial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate fill-length cDNA clones of interest (Lerner, R.A. *Adv. Immunol.* 36:1 (1984); Maniatis).

The enzymes and gene products of the instant 17 kb nucleic acid fragment may be produced in heterologous host cells, particularly in the cells of microbial hosts, and can be used to prepare antibodies to the resulting proteins by methods well known to those skilled in the art. The antibodies are useful for detecting the proteins in situ in cells or in vitro in cell extracts. Preferred heterologous host cells for production of the instant enzymes are microbial hosts. Microbial expression systems and expression vectors containing regulatory sequences that direct high level expression of foreign proteins are well known to those skilled in the art. Any of these could be used to construct chimeric oenes for production of the any of the gene products of the 17 kb fragment. These chimeric genes could then be introduced into appropriate microorganisms via transformation to provide high level expression of the enzymes.

Additionally, chimeric genes will be effective in altering the properties of the host bacteria. It is expected, for example, that introduction of chimeric genes encoding one or more of the ORF's 5, 6, 10, 12 and 13 under the control of the appropriate promoters, into a host cell comprising at least one copy of these genes will demonstrate the ability to convert cyclohexanol to cyclohexanone, cyclohexanone to ε-caprolactone; ε-caprolactone to 6-alcohol hexanonic acid; 6-alcohol hexanonic acid to 6-aldehyde hexanoic acid; and 6-aldehyde hexanoic acid to adipic acid respectively. Additionally expression of ORF's 1–4, 7–9, and 11, either separately or together may facilitate the mediation of cyclohexanol to adipic acid, or any of the intermediate steps depending on the presence or absence of these proteins in the host.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $1P_L$, $1P_R$, T7, tac, and trc (useful for expression in *Escherichia coli*).

Termination control regions may also be derived from various genes native to the preferred hosts. Optionally, a termination site may be unnecessary, however, it is most preferred if included.

All or a portion of the nucleic acid fragments of the instant invention may also be used as probes for genetically and physically mapping the genes that they are a part of, and as markers for traits linked to expression of the instant enzymes. For example, the instant nucleic acid fragments may be used as restriction fragment length polymorphism (RFLP) markers. Southern blots (Maniatis) of restriction-digested bacterial genomic DNA may be probed with the nucleic acid fragments of the instant invention. The resulting banding patterns may then be subjected to genetic analyses using computer programs such as MapMaker (Lander et at., *Genomics* 1:174–181 (1987)) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. *Am. J. Hum. Genet.* 32:314–331 (1980)).

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art.

DESCRIPTION OF THE PREFERRED EMBODIMENTS

The present invention relates to the isolation of genes encoding enzymes useful for the conversion of cyclohexanol to adipic acid. The relevant genes were isolated from an Acinetobacter sp. which was cultured from an industrial waste stream. Colonies that had the ability to grow on cyclohexanol as a sole carbon source were selected for further study.

In order to isolate the relevant adipic acid synthesizing genes, a cosmid library was prepared from the isolated Acinetobacter sp colonies. The cosmid library was screened for a gene encoding a monooxygenase enzyme known to be resent in the cyclohexanol degradation pathway. Screening was done with PCR rimers generated from the known monooxygenase sequence. Positive clones ontained inserts of 35–40 kb, containing homology to the monooxygenase gene. Further sequencing identified 13 open reading frames (ORF) on a 17 kb fragment. The sequences of ORF's 5, 6, 10, 12 and 13 produced deduced gene products that, in combination, provided the necessary enzymes for the conversion of cyclohexanol to adipic acid. Transformed hosts containing the 17 kb fragment demonstrated the ability to produce adipic acid from cyclohexanol, confirming the stated utility.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

GENERAL METHODS

Procedures for phosphorylations, ligations and transformations are well known in the art. Techniques suitable for use in the following examples may be found in Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis").

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Bacterial Strains And Plasmids:

Acinetobacter sp. SE19 was isolated from enrichment of activated sludge obtained from an industrial wastewater treatment facility. *Escherichia coli* XL1-BlueMR and Super-Cos 1 cosmid vector were purchased as part of the SuperCos 1 Cosmid Vector Kit from Stratagene (La Jolla, Calif.). Max Efficiency competent cells of *E. coli* DH5α was purchased from GIBCO/BRL (Gaithersburg, Md.). Shot-gun cloning vector pUC18 treated with SmaI/BAP was also purchased from GIBCO/BRL.

Growth Conditions:

Bacterial cells were usually grown in Luria-Bertani medium containing 1% of bacto-tryptone, 0.5% of bacto-yeast extract and 1% of NaCI unless otherwise indicated below.

Synthetic S12 medium was used to establish enrichment. S12 medium contains the following: 10 mM ammonium sulfate, 50 mM potassium phosphate buffer (pH 7.0), 2 mM $MgCl_2$, 0.7 mM $CaCl_2$, 50 uM $MnCl_2$, 1 uM $FeCl_3$, 1 uM $ZnCl_3$, 1.72 uM $CuSO_4$, 2.53 uM $CoCl_2$, 2.42 uM $Na_2MoO_2$, and 0.0001% $FeSO_4$. The carbon sources were added directly to the S12 medium and the bacteria were grown in sealed culture flasks.

S12 agar was used to test isolates that use compounds as the sole source of carbon and energy. S12 agar was prepared by adding 1.5% Noble agar (DIFCO) to S12 medium. Bacteria growing on S12 agar were supplied with cyclopentanol or other volatile compounds as vapor by placing 5 uL of a volatile compound on the interior of the petri dish lid. The petri dish was sealed with parafilm and incubated with the lid on the bottom.

The standard M9 minimal medium was used to assay for adipic acid production from *E. coli* cosmid clones. The M9 medium consisted of 42.3 mM $Na_2HPO_4$, 22.1 mM $KH_2PO_4$, 8.6 mM NaCl, 18.7 mM $NH_4Cl$, 2 mM $MgSO_4$, 0.1 mM $CaCl_2$, 0.4% of glucose was used as the carbon source. Cyclohexanol at 330 ppm was used as the substrate for adipic acid production.

Construction Of Acinetobacter Cosmid Libraries:

Acinetobacter sp. SE19 was grown in 25 ml LB medium for 6 h at 37° C. with aeration. Bacterial cells were centrifuged at 6,000 rpm for 10 min in a Sorvall RC5C centrifuge at 4° C. Supernatant was decanted and cell pellet was frozen at −80° C. Chromosomal DNA was prepared as outlined below with special care taken to avoid shearing of DNA. The cell pellet was gently resuspended in ml of 50 mM Tris- 10 mM EDTA (pH 8) and lysozyme was added to a final concentration of 2 mg/ml. The suspension was incubated at 37° C. for 1 h. Sodium dodecyl sulfate was then added to a final concentration of 1% and proteinase K was added at 100 μg/ml. The suspension was incubated at 55° C. for 2 h. The suspension became clear and the clear lysate was extracted with equal volume of phenol:chloroform:isoamyl alcohol (25:24:1). After centrifuging at 12,000 rpm for 20 min, the aqueous phase was carefully removed and transfered to a new tube. Two volunes of ethanol were added and the DNA was gently spooled with a sealed glass pasteur pipet. The DNA was dipped into a tube containing 70% ethanol. After air drying, the DNA was resuspended in 400 μl of TE (10 mMTris-1 mM EDTA, pH 8) with RNaseA (100 μg/ml) and store at 4° C. The concentration and purity of DNA was determined spectrophotometrically by OD260/OD280. A diluted aliquot of DNA was run on a 0.5% agarose gel to determine the intact nature of DNA.

Chromosomal DNA was partially digested with Sau3A (GIBRO/BRL, Gaithersburg, Md.) as outlined by the instruction manual for the SuperCos 1 Cosmid Vector Kit. DNA (10 μg) was digested with 0.5 unit of Sau3A at room temperature in 100 μl of reaction volume. Aliquotes of 20 μl were withdrawn at various time points of the digestion: e.g., 0, 3, 6, 9, 12 min. DNA loading buffer was added and samples were analyzed on a 0.5% agarose gel to determine the extent of digestion. A decrease in size of chromosomal DNA corresponded to an increase in the length of time for Sau3A digestion. The preparative reaction was performed using 50 μg of DNA digested with 1 unit of Sau3A for 3 min. at room temperature. The digestion was terminated by addition of 8 mM of EDTA. The DNA was extracted once with phenol:chloroform:isoamyl alcohol and once with chloroform. The aqueous phase was adjusted to 0.3 M NaOAc and ethanol precipitated. The partially digested DNA was dephosphorylated with calf intestinal alkaline phosphatase and ligated to SuperCos 1 vector, which had been treated according to the instructions in the SuperCos 1 Cosmid Vector Kit. The ligated DNA was packaged into lamda phage using Gigapack III XL packaging extract recommended by Stratagene. Manufacturer's instructions were followed. The packaged Acinetobacter genomic DNA library contained a phage titer of $5.6 \times 10^4$ colony forming units per μg of DNA as determined by transfecting *E. coli* XL1-Blue MR. Cosmid DNA was isolated from six randomly chosen *E. coli* transfornants and found to contain large insert of DNA (2540 kb).

Construction of Shot-gun Sequencing Libraries:

Cosmid DNA was sheared in a nebulizer (Inhalation Plastics Inc., Chicago, Ill.) at 20 psi for 45 sec and the 1–3 kb portion was gel purified. Purified DNA was treated with T4 DNA polymerase and T4 polynucleotide kinase following manufacturer's (GIBCO/BRL) instructions. Polished inserts were ligated to pUC18 vector using Ready-To-Go pUC18SmaI/BAP+Ligase (GIBCO/BRL). The ligated DNA was transformed into *E. coli* DH5α cells and plated on LB with ampicillin and X-gal. A majority of the transformants were white and those containing inserts were sequenced with the universal and reverse primers of pUC 18 by standard sequencing methods.

Isolation And Identification of Adipic Acid:

Cells thought to contain adipic acid were prepared for adipic acid analysis by freez-thawing, and filtration. Supernatant was subjected to HPLC analysis of adipid acid.

The HPLC system used was a Hewlett Packard 1100 series with photo diode array detector. HPLC organic acid analysis column (Aminex HPX-87H ion exclusion column, 300 mm×7.8 mm) was purchase from BioRad. The column temperature was controled at 40° C. The mobile phase was 0.004 M sulfuric acid at a flow rate of 0.6 ml/min. 100 µl of samples were injected and 210 nm was used for detection. Standard samples were prepared with known amounts of adipic acid in the medium. The retention time of adipic acid produced were compared to that of the authentic standard.

Electrospray LC/MS analysis was used to confirm or refute the presence of adipic acid in the samples. The method couples the reverse phase HPLC with a Prodigy C18 column on a Hewlett Packard 1100 machine to a Finnigan TSQ-700 mass spectrometer. The mobile phase for the HPLC was a 10 min linear gradient of 20% solvent containing acetonitrile and 0.5% acetic acid to 90% of the same solvent. The flow rate was 0.25 ml/min, with post column 50:1 splitter yielding ultimate flow to the mass spectrometer of 5 µl/min. The electrospray mass spectrometry was conducted in negative ion detection mode with scan width of 123–400 da. Confirmation of adipic acid in a sample requires the detection of peak containing 145 amu ion at the experimentally determined retention time for adipic acid.

Example 1
Isolation Of Acinetobacter Sp. From An Industrial Wastestream

Sludge was obtained from an industrial wastestrearn and bacteria were isolated from a cyclopentanol enrichment culture. Analysis of 16s rRNA gene sequences indicated that the collection of isolates included members of the bacterial genus Acinetobacter.

Bacteria described in this invention that grow on cyclohexanol were isolated from a cyclopentanol enrichment culture. The enrichment culture was established by inoculating 1 mL of activated sludge into 20 mL of S12 medium in a 125 mL screw-cap Erlenmeyer flask. The enrichment culture was supplemented with 100 ppm cyclopentanol added directly to the culture medium and was incubated at 35° C. with reciprocal shaking. The enrichment culture was maintained by adding 100 ppm cyclopentanol every 2–3 days. The culture was diluted every 2–10 days by replacing 10 mL of the culture with the same volume of S12 medium. After 15 days of incubation, serial dilutions of the enrichment ulture were spread onto LB plates. Single colonies were screened for the ability to grow on S12 liquid with cyclohexanol as the sole carbon and energy source.

The cultures were grown at 35° C. in sealed tubes. One of the isolates, SE19 was selected for further characterization.

The 16s rRNA genes of SE19 isolates were amplified by PCR and analyzed as follows. SE19 was grown on LB agar. Several colonies from the plate were suspended in 200 mL of lysis buffer (1% Triton X-100, 20 mM Tris (pH 8.5), 2 mM EDTA). The mixture was heated to 95° C. for 10 min and then centrifuged to remove cellular debris. The 16s rRNA gene sequences in the supernatant were amplified by PCR by using a commercial kit according to the manufacturer's instructions (Perkin Elmer) with HK12 primer GAG TTT GAT CCT GGC TCA G (SEQ ID NO:28) and HK13 primer TAC CTT GTT ACG ACT T (SEQ ID NO:29). PCR was performed in a Perkin Elmer GeneAmp 9600. The samples were incubated for 5 min at 94° C. and then cycled 35 times at 94° C. for 30 sec, 55° C. for 1 min and 72° C. for 1 min. The amplified 16s rRNA genes were purified using a QIAquick PCR Purification Kit according to the manufacturer's instructions (Qiagen) and sequenced on an automated ABI sequencer. The sequencing reactions were initiated with HK 12 primer, HK 13 primer and HK 14 primer GTG CCA GCA GYM GCG GT; Y=C OR T, M=A OR C (SEQ ID NO:30). The 16s rRNA gene sequence of each isolate was used as the query sequence for a BLASTN search (Altschul, Stephen F., Thomas L. Madden, Alejandro A. Schaffer,Jinghui Zhang, Zheng Zhang, Webb Miller, and David J. Lipman (1997), "Gapped BLAST and PSI-BLAST: a new generation of protein database search programs", Nucleic Acids Res. 25:3389–3402. The BlastN result of all isolates showed that SE19 has close homology to *Acinetobacter haemolyticus* and *Acinetobacter junii*, 99% nucleotide identity to each.

Example 2

Identification and Characterization of Cosmid Clones Containing Cyclohexanone Monooxypenase Gene The cosmid library of Acinetobacter SE19 was screened based on the homology of the cyclohexanone monooxygenase gene. Two primers, monoL: GAGTCTGAGCATATGT-CACAAAAAATGGATTTTG (SEQ ID NO:31) monoR: GAGTCTGAGGGATCCTTAGGCATTG-GCAGGTTGCTTGAT (SEQ ID NO:32) were designed based on the published sequence of cyclohexanone monooxygenase gene ofAcinetobacter sp. NCIB 9871. The cosmid library was screened by PCR using monoL and monoR primers. Five positive clones (5B12, SF5, 8F6, 14B3 and 14D7) were identified among about 1000 clones screened. They all contain inserts of 35–40 kb that show homology to the cyclohexanone monooxygenase gene amplified by monoL and monoR primers. Southern hybridization using this gene fragment as a probe indicated that the cosmid clone 5B12 has about 20 kb region upstream of the monooxygenase gene and cosmid clone 8F6 has about 30 kb downstream of the monooxygenase gene. Cosmid clone 14B3 contains rearranged Acinetobacter DNA adjacent to the monooxygenase gene. Shot gun libraries of 5B12 and 8F6 were constructed and inserts were sequenced with pUC18 universal and reverse primers. Sequences of 200–300 clones from each library were assembled using Sequencher 3.0 program and a contig of 17419 bp containing the cyclohexanone monooxygenase gene was formed.

ORF's 1–13 from the 17 kb gene cluster were identified by conducting BLAST (Basic Local Aligrnment Search Tool; Altschul, S. F., et al., (1993) *J. Mol. Biol.* 215:403410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, SWISS-PROT protein sequence database, EMBL, and DDBJ databases). The sequences obtained were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI.

The sequence comparisons based on BLASTX analysis against the "nr" database are given below in Table 1 using Xnr BLAST algorithm.

TABLE 1

| ORF | Gene Name | Similarity Identified | SEQ ID base | SEQ ID Peptide | % Identity[a] | % Similarity[b] | E-value[c] |
|---|---|---|---|---|---|---|---|
| 1 | fadC | Sp\|P45856\|MMGB_BACSU 3-Hydroxybutyryl-CoA Dehydrogenase [*Bacillus Subtilis*] | 1 | 2 | 36 | 51 | 4e-39 |
| 2 | fadB | Gi\|3253197 (AF029714) PhaA [*Pseudomonas Putida*] | 3 | 4 | 48 | 64 | 1e-60 |
| 3 | fadE | Sp\|P45857\|ACDB_BACSU Acyl-CoA Dehydrogenase [*Bacillus Subtilis*] | 5 | 6 | 42 | 59 | 2e-77 |
| 4 | etfD | SP\|P94132\|ETFD_ACICA Ubiquinone Oxidoreductase [*Acinetobacter Calcoaceticus*] | 7 | 8 | 91 | 95 | 0.0 |
| 5 | chdA | Sp\|P12015\|CYMO_ACISP Cyclohexanone Monooxygenase [Acinetobacter Sp.] | 9 | 10 | 97 | 97 | 0.0 |
| 6 | chdB | Gi\|1790871 (U32622) Toluenesulfonate Aldehyde Dehydrogenase [*comamonas Testosteroni*] | 11 | 12 | 38 | 57 | e-105 |
| 7 | chdR | gnl\|PID\|e1182174 (Z99105) AraC-like transcriptional regulator [*Bacillus subtilis*] | 13 | 14 | 34 | 54 | 7e-10 |
| 8 | chdZ | PID\|g282086\|PIR: locus S27482 hypothetical protein 1 - [*Actinobacillus pleuropneumoniae.*] | 15 | 16 | 75 | 85 | 2e-99 |
| 9 | chdY | PID\|g130250\|SWISS-PROT: locus PIV_MORBO, accession P20665: Pilin Gene Inverting Protein [*Moraxella bovis*] | 17 | 18 | 29 | 48 | 2e-37 |
| 10 | chdC | PID\|g1708335\|SWISS-PROT: locus LINC_PSEPA, accession P50197 2,5-Dichloro-2,5-Cyclohexadiene-1,4-Diol Dehydrogenase [*Sphingomonas paucimobilis*] | 19 | 20 | 41 | 58 | 2e-47 |
| 11 | chdX | PID\|g1778844 \|GENBANK: locus DDU83086, accession U83086: LimA [*Dictyostelium discoideum*] | 21 | 22 | | | 0.26 |
| 12 | chdD | PID\|g728808\|SWISS-PROT: locus ADH1_SULSO, accession P39462: NAD-Dependent Alcohol Dehydrogenase [*Sulfolobus solfataricus*] | 23 | 24 | 32 | 52 | 1e-60 |
| 13 | chdE | PID\|g1352065\|SWISS-PROT: locus BAH_STRHY, accession Q01109: Acetyl-Hydrolase [*Streptomyces hygroscopicus*] | 25 | 26 | 36 | 51 | 2e-32 |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

BLAST results indicated that the sequence with the greatest homology to ORF5 encoding the monooxygenase was 97% identical and 97% similar to the gene published by Chen et al. *J. Bacteriol.* 170 (2), 781–789 (1988). The sequence with the greatest homology to ORF6 encoding the enzyme responsible for the conversion of 6-aldehyde hexanoic acid to adipic acid was 38% identical and 57% similar to the gene published by Junker et al., *J. Bacteriol.* 179 (3), 919–927 (1997). The sequence with the greatest homology to ORFl0 encoding the enzyme responsible for the conversion of cyclohexanol to cyclohexanone was 41% identical and 58% similar to the gene published by Nagata et al., *J. Bacteriol.* 176 (11), 3117–3125 (1994). The sequence with the greatest homology to ORF 12 encoding the enzyme responsible for the conversion of 6-alcohol hexanoic acid to 6-aldehyde hexanoic acid was 32% identical and 52% similar to the gene published by Ammendola et al., *Biochemistry* 31 (49), 12514–12523 (1992). The sequence with the greatest homology to ORF 13 encoding the enzyme responsible for the conversion of caprolactone to 6-hexanoic acid was 36% identical and 51% similar to the gene published by Raibaud et al., *J. Bacteriol.* 173 (14), 4454–4463 (1991).

Example 3

Conversion of Cyclohexanol to Adipic Acid by *E. coli* Cosmid Clones

Five *E. coli* cosmid clones containing the gene cluster and the *E. coli* strain containing the supercos vector control were grown in M9 minimal medium supplemented with 0.4% glucose as the carbon source. Cells were grown at 30° C. with shaking for 2 h and 330 ppm of cyclohexanol was added. Cells were further incubated at 30° C. and 1 ml of samples were taken 2 h, 4 h and 20 h after addition of cyclohexanol. Control culture consisted of the host strains transformed only with the supercos vector was grown under the same conditions.

Samples were frozen at −80° C. and thawed at 37° C. Freeze-thawing was repeated three times. Cells were pelleted and supernatants were passed through 0.22 μm disc filters. The filtered supernatants were analyzed by HPLC, as described above.

Figure 3:
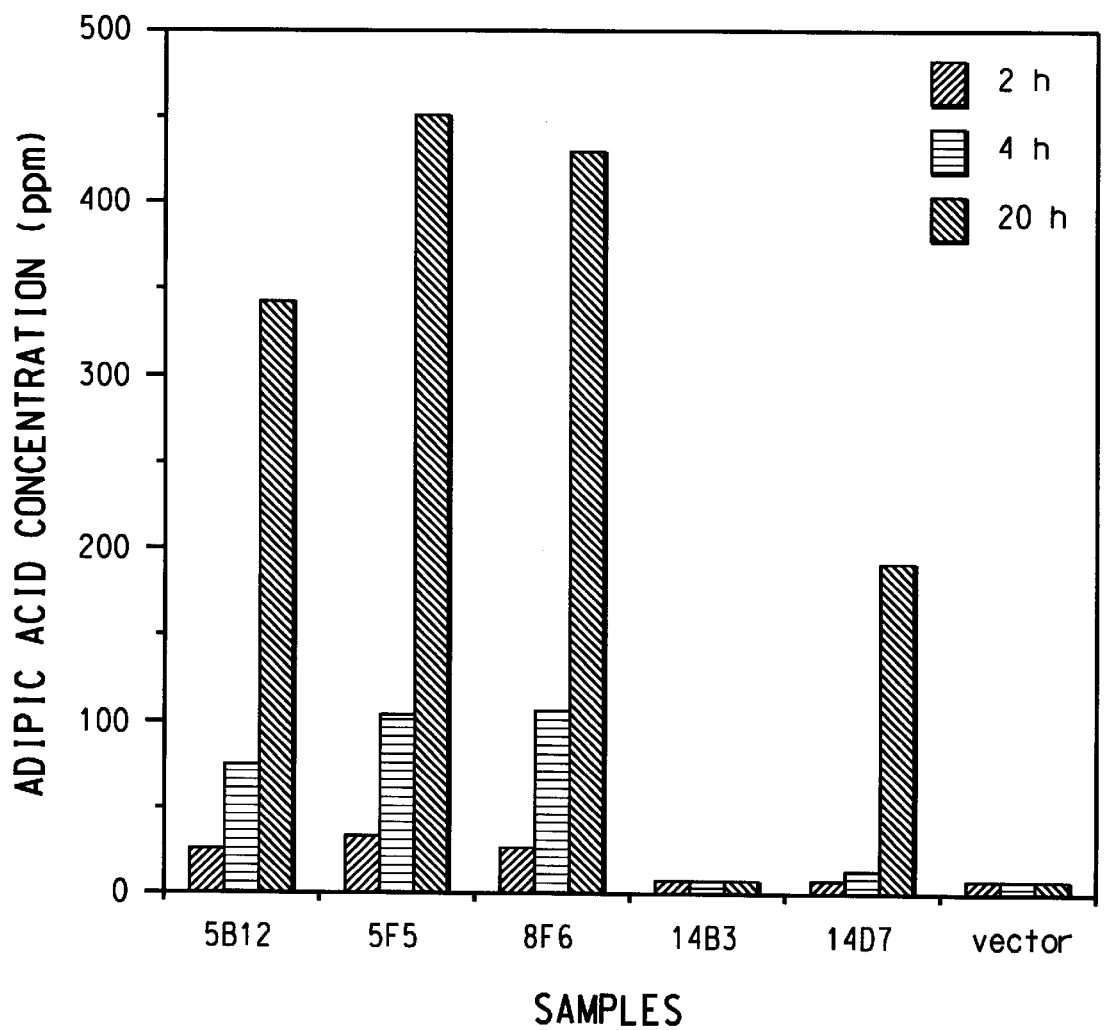
FIG. 3 is a diagram showing the amount of adipic acid produced from the recombinant E. coli cosmid clones.

Four out of five cosmid clones 5B12, 5F5, 8F6 and 14D7 tested positive for adipic acid production. The amount of adipic acid produced was seen to increase with time (FIG. 3). One cosmid clone 14B3 showed no adipic acid production (equivalent to the vector control), even after 20 h growth. The rearranged Acinetobacter chromosomal DNA flanking the monooxygenase gene region revealed by Southern hybridization in 14B3 accounted for the no production of adipic acid. The adipic acid detected in the positive cosmid clones was estimated to be 200–400 ppm on the basis of HPLC analysis. The supercos control was negative for adipic acid production with the estimated detection limit of <10 ppm.

Conversion of cyclohexanol to adipic acid by E. coli cosmid clones was also confirmed by electrospray LC/MS analysis. The major ion observed in the negative ion electrospray mass spectrum of the adipic acid peak eluted at the expected retension time appears at 145 amu, which agrees with the molecular weight of the deprotonated adipic acid.

What is claimed is:

1. An isolated nucleic acid fragment encoding adipic acid synthesizing enzymes selected from the group consisting of:
   (a) an isolated nucleic acid molecule as set forth in SEQ ID NO:27;
   (b) an isolated nucleic acid molecule that hybridizes with (a) under the following hybridization conditions: 0.1× SSC, 0.1% SDS at 65° C.; and washed with 2×SSC, 0.1% SDS followed by 0.1×SSC, 0.1% SDS; or
   an isolated nucleic acid molecule that is completely complementary to (a) or (b);

wherein the isolated nucleic acid molecule of parts (a) or (b) comprises open reading frames encoding each of the enzymes selected from the group consisting of:
   a cyclohexanone monooxygenase, a 6-aldehyde hexanoic dehydrogenase, a cyclohexanol dehydrogenase, a 6-hydroxy hexanoic acid dehydrogenase and a caprolactone hydrolase.

* * * * *